US007189524B1

(12) United States Patent
An et al.

(10) Patent No.: US 7,189,524 B1
(45) Date of Patent: Mar. 13, 2007

(54) RECEPTOR LIGANDS AND METHODS OF MODULATING RECEPTORS

(75) Inventors: Songzhu An, San Carlos, CA (US); Jin-Long Chen, San Mateo, CA (US); Hui Tian, Foster City, CA (US); Wendy Wen Zhong, Daly City, CA (US)

(73) Assignee: Amgen, Inc., Thousand Oaks, CA (US)

( * ) Notice: Subject to any disclaimer, the term of this patent is extended or adjusted under 35 U.S.C. 154(b) by 87 days.

(21) Appl. No.: 10/719,692

(22) Filed: Nov. 21, 2003

Related U.S. Application Data

(60) Provisional application No. 60/421,142, filed on Nov. 25, 2002, provisional application No. 60/444,153, filed on Jan. 30, 2003.

(51) Int. Cl.
*G01N 33/566* (2006.01)
(52) U.S. Cl. .................................. 435/7.21; 436/501
(58) Field of Classification Search ............... None
See application file for complete search history.

(56) References Cited

U.S. PATENT DOCUMENTS

| 6,500,938 B1 | 12/2002 | Au-Young et al. |
| 6,555,339 B1 | 4/2003 | Liaw et al. |
| 2002/0052022 A1 | 5/2002 | Elshourbagy et al. |

FOREIGN PATENT DOCUMENTS

| WO | WO 98/56820 A1 | 12/1998 |
| WO | WO 00/22129 A1 | 4/2000 |
| WO | WO 01/36471 A2 | 5/2001 |
| WO | WO 01/36473 A2 | 5/2001 |
| WO | WO 01/73029 A2 | 10/2001 |
| WO | WO 01/74904 A2 | 10/2001 |
| WO | WO 01/77320 A2 | 10/2001 |
| WO | WO 01/77326 A1 | 10/2001 |
| WO | WO 01/87937 A2 | 11/2001 |
| WO | WO 01/94385 A2 | 12/2001 |
| WO | WO 01/94629 A2 | 12/2001 |
| WO | WO 01/98330 A2 | 12/2001 |
| WO | WO 02/02767 A1 | 1/2002 |
| WO | WO 02/06466 A1 | 1/2002 |
| WO | WO 02/13845 A2 | 2/2002 |
| WO | WO 02/18579 A2 | 3/2002 |
| WO | WO 02/18938 A1 | 3/2002 |
| WO | WO 02/28999 A2 | 4/2002 |
| WO | WO 02/061087 A2 | 8/2002 |
| WO | WO 02/072755 A2 | 9/2002 |
| WO | WO 02/084298 A2 | 10/2002 |
| WO | WO 03/021262 A1 | 3/2003 |

OTHER PUBLICATIONS

Aktories, K., et al., "Nicotinic Acid Inhibits Adipocyte Adenylate Cyclase in a Hormone-Like Manner", *Elsevier/North-Holland Biomedical Press* (Jun. 1980), vol. 115, No. 1, pp. 11-14.
Baldwin, G., et al., "Gut Hormones, Growth and Malignancy", *Bailliére's Clinical Endocrinology and Metabolism* (Jan. 1994), vol. 8, No. 1, pp. 185-214).
Berridge, M., et al., "Inositol Trisphospate, a Novel Second Messenger in Cellular Signal Transduction", *Nature* (Nov. 22, 1984), vol. 312, pp. 315-321.
Brown, M., et al., *Drugs Used in the Treatment of Hyperlipoproteinemias*, Goodman and Gillman (1990) 8th Ed., Ch. 36, pp. 889-891.
Brown, W., et al., "Nicotinic Acid and its Derivatives", Medical Research Foundation, Washington, D.C., pp. 189-213.
Buck, L., et al., "A Novel Multigene Family May Encode Odorant Receptors: A Molecular Basis for Odor Recognition", *Cell*, (Apr. 5, 1991), vol. 65, pp. 175-187.
Dipalma, J., et al., "Use of Niacin as a Drug", *Annual Review of Nutrition* (1991), vol. 11, pp. 169-187.
Felley-Bosco, E., et al., "Constitutive Expression of Inducible Nitric Oxide Synthase in Human Bronchial Epithelial Cells Induces c-*fos* and Stimulates the cGMP Pathway", *American Journal of Respiratory Cell and Molecular Biology* (1994), vol. 11, pp. 159-164.
Fong, T., "Mechanistic Hypotheses for the Activation of G-Protein-Coupled Receptors", *Cell Signal* (1996), vol. 8, No. 3, pp. 217-224.
Gey, K., et al., eds., *Metabolic Effects of Nicotinic Acid and its Derivatives*, Proceedings from Workshop on the Metabolic Effects of Nicotinic Acid and its Derivatives, Flims, Switzerland, Mar. 23-25, 1970, (Publisher, Hans Huber, Bern, Switzerland, 1971).
Kaijser, L., et al., "Dissociation of the Effects of Nicotinic Acid on Vasodilatation and Lipolysis by a Prostaglandin Synthesis Inhibitor, Indomethacin, in Man", *Medical Biology* (1979), vol. 57, pp. 114-117.
Lanes, R., et al., "Acipimox, a Nicotinic Acid Analog, Stimulates Growth Hormone Secretion in Short Healthy Prepubertal Children", *Journal of Pediatric Endocrinology & Metabolism* (2000), vol. 13, pp. 1115-1120.
Lee, D., et al., "Discovery and Mapping of Ten Novel G Protein-Coupled Receptor Genes", *Gene* (2001), vol. 275, pp. 83-91.
Lorenzen, A., et al., "Characterization of a G Protein-Coupled Receptor for Nicotinic Acid", *Molecular Pharmacology* (2001), vol. 59, pp. 349-357.
Lorenzen, A., et al., "G Protein-Coupled Receptor for Nicotinic Acid in Mouse Macrophages", *Biochemical Pharmacology* (2002), vol. 64, pp. 645-648.
McIntosh, C., et al., "Glucose-Dependent Insulinotropic Polypeptide Stimulation of Lipotysis in Differentiated 3T3-L1 Cells: Wortmannin-Sensitive Inhibition by Insulin", *Endocrinology* (1999), vol. 140, No. 1, pp. 398-404.
Miyai, K., et al., "Synthesis and Antiinflammatory Activity of 6-Oxo-1-(β-D-ribofuranosyl)nicotinic Acid and Related Derivatives", *Journal of Medicinal Chemistry* (1978), vol. 21, No. 5, pp. 427-430.
Monzon, J, "Lipolysis in Adipocytes Isolated from Deep and Superficial Subcutaneous Adipose Tissue", *Obesity Research* (Apr. 2002), vol. 10, No. 4, pp. 266-269.
Morris, A., et al., "Physiological Regulation of G Protein-Linked Signaling", *Physiological Reviews* (Oct. 1999), vol. 79, No. 4, pp. 1373-1430.

(Continued)

*Primary Examiner*—John Ulm
(74) *Attorney, Agent, or Firm*—Banner & Witcoff

(57) ABSTRACT

The invention provides natural ligands of TGR183 receptors and methods of identifying modulators of various TGR183 receptors using the ligands. Methods of using the modulators to treat diseases or disorders associated with dysfunction of the TGR183 receptor are also provided.

4 Claims, 8 Drawing Sheets

OTHER PUBLICATIONS

Nomura, H., et al., "Molecular Cloning of cDNAs Encoding a LD78 Receptor and Putative Leukocyte Chemotactic Peptide Receptors", *International Immunology* (1993), vol. 5, No. 10, pp. 1239-1249.

Offermanns, S., et al., "$G\alpha_{15}$ and $G\alpha_{16}$ Couple a Wide Variety of Receptors to Phospholipase C", *The Journal of Biological Chemistry* (Jun. 23, 1995), vol. 270, No. 25, pp. 15175-15180.

Schaub, A, et al., "PUMA-G, and IFN-γ-inducible Gene in Macrophages is a Novel Member of the Seven Transmembrane Spanning Receptor Superfamily", *European Journal of Immunology* (2001), vol. 31, pp. 3714-3725.

Stables, J., et al., "A Bioluminescent Assay for Agonist Activity at Potentially Any G-Protein-Coupled Receptor", *Analytical Biochemistry* (1997), vol. 252, pp. 115-126.

Wilkie, T., et al., "Characterization of G-protien α subunits in the $G_\alpha$ Class: Expression in Murine Tissues and in Stromal and Hematopoietic Cell Lines", *Proceedings of the National Academy of Sciences of the United States of America* (Nov. 1991), vol. 88., pp. 10049-10053.

FIGURE 1

```
MNRHHLQDHFLE I DKKNCCVFRDDF I AKVLPPVLG LEF I FGLLGNGLALW I FCFHLKSWKS SR I LFNLAVADFLL I I CL
              MYNGSCC R I EGDT I SQVMPPLL I VAEVLGALGNGVALC GFCFHMKTWKPST VYLFNLAVADFLLMI CL

PFVMDYYVRRS DWNFGD I PCRLV LFMFAMNRQGS I I FLTVVAVDRYFRVVHPHHALNK I SNWTAA I I SCLLWG I TVGLTV
PFRTDYYLRRR HWAFGD I PCRV GLFTLAMNRAGS I VFLTVVAADRYFKVVHPHHAVNT I STRVAAG I VCTLWALV I LGTV

HLLKKLL I QNGPANVC I SF S I I CHT FRWHEAMFLLEFLL PLG I I LFCSAR I I WSLRQRQ - MDRHAK I KRA I TF I MVVAI V
YLLLENHLCVQETAVSCESF I MESI ANGWHD I MFQLEFFMPLG I I LFCSFK I VWSLRRRQQLARQARMKKATRF I MVVAI V

FV I CFLPSVVVR I R I FWLLHTSGTQNCEVYR SVDLAFF I TLSFTYMNSMLDPVVYYFSSPSFPNFFSTL I NRCLQRKMTG
F I TCYLPSVSARLYFLWTVPSS - - - - ACDPSVHGAL H I TLSFTYMNSMLDPLVYYFSSPSFPKFYNKLK I CSLKPKQPG

EPDNNRSTSVELTGDPNK - TRGAPEALMANSGEPWSPSYLGPTSNNHSKKGHCHQEPASLEKQLGCC I E
HSKTQRPEEMP I SNLGRRSC I SVANSFQSQSDGQWDPH I VEWH
```

FIGURE 5

Mouse adipocytes pre-adipocyte (L1) +/−
differentiated +/−
differentiated-BRL +/−

Human adipocytes adipocyte, primary +/−
pre-adipocyte, cultured +/−
adipocyte, cultured +/−

TGR183

RT

FIGURE 6
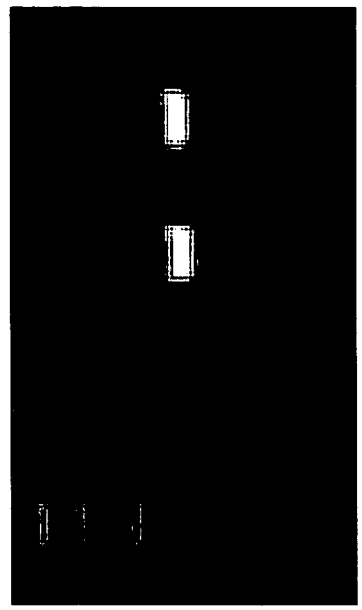
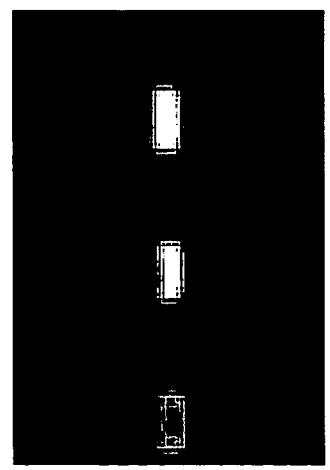

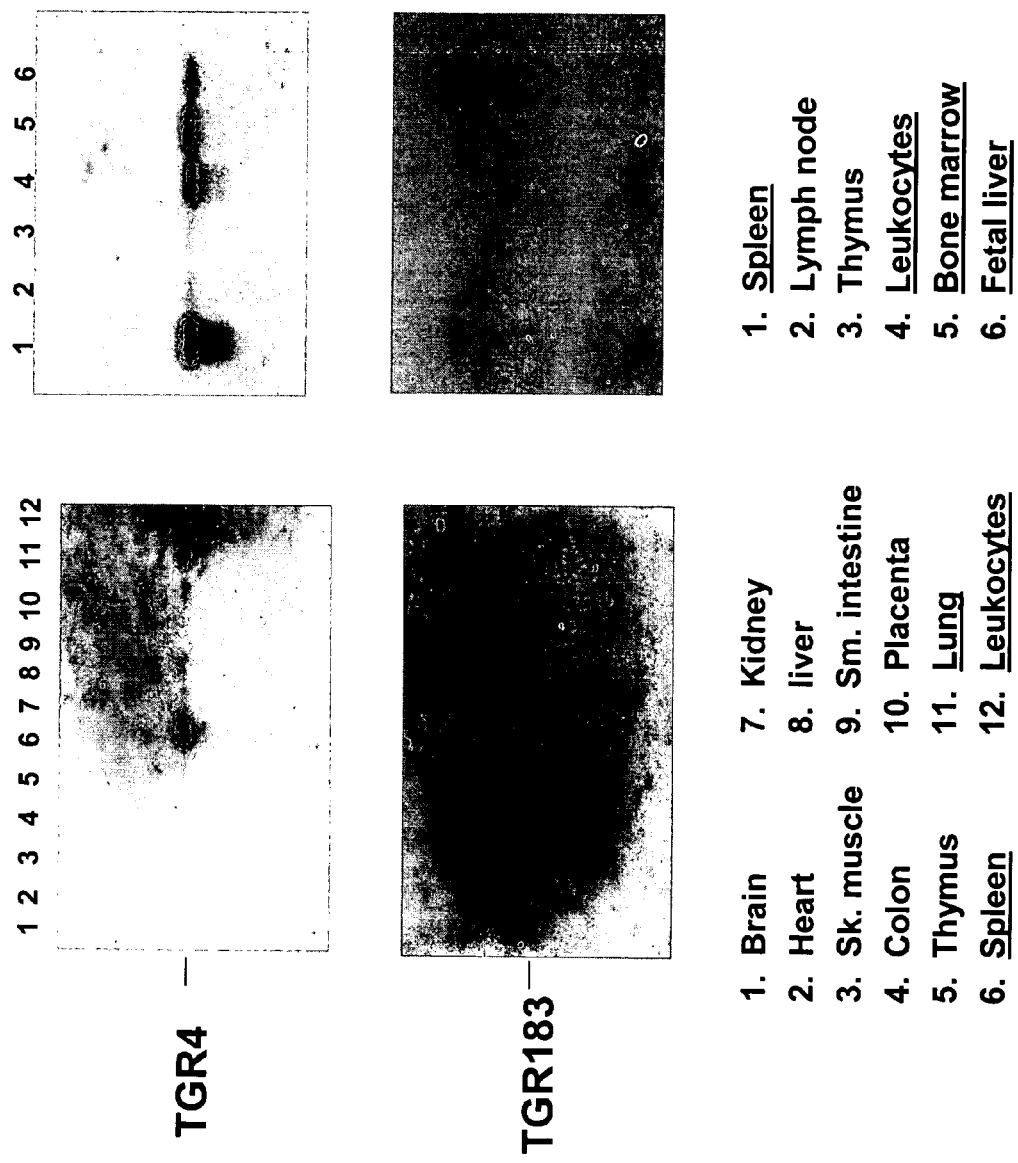
Fig. 8. Differential Expression between TGR4 and TGR183

SEQUENCE LISTING

<160> NUMBER OF SEQ ID NOS: 9

<210> SEQ ID NO 1
<211> LENGTH: 1164
<212> TYPE: DNA
<213> ORGANISM: Homo sapiens
<220> FEATURE:
<223> OTHER INFORMATION: human G-protein coupled receptor TGR4a (HM74)

<400> SEQUENCE: 1

```
atgaatcggc accatctgca ggatcacttt ctggaaatag acaagaagaa ctgctgtgtg      60
ttccgagatg acttcattgc caaggtgttg ccgccggtgt tggggctgga gtttatcttt     120
gggcttctgg gcaatggcct tgccctgtgg attttctgtt tccacctcaa gtcctggaaa     180
tccagccgga ttttcctgtt caacctggca gtagctgact tctactgat catctgcctg      240 ccgttcgtga tggactacta tgtgcggcgt tcagactgga actttgggga catcccttgc     300
cggctggtgc tcttcatgtt tgccatgaac cgccagggca gcatcatctt cctcacggtg     360
gtggcggtag acaggtattt ccgggtggtc catccccacc acgccctgaa caagatctcc     420
aattggacag cagccatcat ctcttgcctt ctgtggggca tcactgttgg cctaacagtc     480
cacctcctga agaagaagtt gctgatccag aatggccctg caaatgtgtg catcagcttc     540
agcatctgcc ataccttccg gtggcacgaa gctatgttcc tcctggagtt cctcctgccc     600
ctgggcatca tcctgttctg ctcagccaga attatctgga gcctgcggca gagacaaatg     660
gaccggcatg ccaagatcaa gagagccatc accttcatca tggtggtggc catcgtcttt     720
gtcatctgct tccttcccag cgtggttgtg cggatccgca tcttctggct cctgcacact     780
tcgggcacgc agaattgtga agtgtaccgc tcggtggacc tggcgttctt tatcactctc     840
agcttcacct acatgaacag catgctggac cccgtggtgt actacttctc cagcccatcc     900
tttcccaact tcttctccac tttgatcaac cgctgcctcc agaggaagat gacaggtgag     960
ccagataata accgcagcac gagcgtcgag ctcacagggg accccaacaa aaccagaggc    1020
```

```
gctccagagg cgttaatggc caactccggt gagccatgga gcccctctta tctgggccca    1080
acctcaaata accattccaa gaagggacat tgtcaccaag aaccagcatc tctggagaaa    1140
cagttgggct gttgcatcga gtaa                                           1164
```

<210> SEQ ID NO 2
<211> LENGTH: 387
<212> TYPE: PRT
<213> ORGANISM: Homo sapiens
<220> FEATURE:
<223> OTHER INFORMATION: human G-protein coupled receptor TGR4a (HM74)

<400> SEQUENCE: 2

```
Met Asn Arg His His Leu Gln Asp His Phe Leu Glu Ile Asp Lys Lys
  1               5                  10                  15

Asn Cys Cys Val Phe Arg Asp Asp Phe Ile Ala Lys Val Leu Pro Pro
                 20                  25                  30

Val Leu Gly Leu Glu Phe Ile Phe Gly Leu Leu Gly Asn Gly Leu Ala
             35                  40                  45

Leu Trp Ile Phe Cys Phe His Leu Lys Ser Trp Lys Ser Ser Arg Ile
         50                  55                  60

Phe Leu Phe Asn Leu Ala Val Ala Asp Phe Leu Leu Ile Ile Cys Leu
 65                  70                  75                  80

Pro Phe Val Met Asp Tyr Tyr Val Arg Arg Ser Asp Trp Asn Phe Gly
                 85                  90                  95

Asp Ile Pro Cys Arg Leu Val Leu Phe Met Phe Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Trp Thr Ala
    130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335
```

```
Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
    370                 375                 380

Cys Ile Glu
385

<210> SEQ ID NO 3
<211> LENGTH: 1092
<212> TYPE: DNA
<213> ORGANISM: Homo sapiens
<220> FEATURE:
<223> OTHER INFORMATION: human G-protein coupled receptor TGR4b

<400> SEQUENCE: 3
atgaatcggc accatctgca ggatcacttt ctggaaatag acaagaagaa ctgctgtgtg    60
ttccgagatg acttcattgt caaggtgttg ccgccggtgt tggggctgga gtttatcttc   120
gggcttctgg gcaatggcct tgccctgtgg attttctgtt ccacctcaa gtcctggaaa    180 tccagccgga ttttcctgtt caacctggca gtggctgact tctactgat catctgcctg    240 cccttcctga tggacaacta tgtgaggcgt tgggactgga gtttggggga catcccttgc   300
cggctgatgc tcttcatgtt ggctatgaac cgccagggca gcatcatctt cctcacggtg   360
gtggcggtag acaggtattt ccgggtggtc catccccacc acgccctgaa caagatctcc   420
aatcggacag cagccatcat ctcttgcctt ctgtggggca tcactattgg cctgacagtc   480
cacctcctga gaagaagat gccgatccag aatggcggtg caaatttgtg cagcagcttc   540
agcatctgcc ataccttcca gtggcacgaa gccatgttcc tcctggagtt cttcctgccc   600
ctgggcatca tcctgttctg ctcagccaga attatctgga gcctgcggca gagacaaatg   660
gaccggcatg ccaagatcaa gagagccatc accttcatca tggtggtggc catcgtctt    720 gtcatctgct tccttcccag cgtggttgtg cggatccgca tcttctggct cctgcacact   780
tcgggcacgc agaattgtga agtgtaccgc tcggtggacc tggcgttctt tatcactctc   840
agcttcacct acatgaacag catgctggac ccgtggtgt actacttctc agcccatcc    900 tttcccaact tcttctccac tttgatcaac cgctgcctcc agaggaagat gacaggtgag   960
ccagataata accgcagcac gagcgtcgag ctcacagggg accccaacaa accagaggc   1020 gctccagagg cgttaatggc caactccggt gagccatgga gccctctta tctgggccca   1080 acctctcctt aa                                                       1092

<210> SEQ ID NO 4
<211> LENGTH: 363
<212> TYPE: PRT
<213> ORGANISM: Homo sapiens
<220> FEATURE:
<223> OTHER INFORMATION: human G-protein coupled receptor TGR4b

<400> SEQUENCE: 4

Met Asn Arg His His Leu Gln Asp His Phe Leu Glu Ile Asp Lys Lys
  1               5                  10                  15

Asn Cys Cys Val Phe Arg Asp Asp Phe Ile Val Lys Val Leu Pro Pro
                 20                  25                  30

Val Leu Gly Leu Glu Phe Ile Phe Gly Leu Leu Gly Asn Gly Leu Ala
             35                  40                  45
```

-continued

```
Leu Trp Ile Phe Cys Phe His Leu Lys Ser Trp Lys Ser Arg Ile
     50                  55                  60

Phe Leu Phe Asn Leu Ala Val Ala Asp Phe Leu Leu Ile Ile Cys Leu
 65                  70                  75                  80

Pro Phe Leu Met Asp Asn Tyr Val Arg Arg Trp Asp Trp Lys Phe Gly
                 85                  90                  95

Asp Ile Pro Cys Arg Leu Met Leu Phe Met Leu Ala Met Asn Arg Gln
                100                 105                 110

Gly Ser Ile Ile Phe Leu Thr Val Val Ala Val Asp Arg Tyr Phe Arg
                115                 120                 125

Val Val His Pro His His Ala Leu Asn Lys Ile Ser Asn Arg Thr Ala
    130                 135                 140

Ala Ile Ile Ser Cys Leu Leu Trp Gly Ile Thr Ile Gly Leu Thr Val
145                 150                 155                 160

His Leu Leu Lys Lys Lys Met Pro Ile Gln Asn Gly Gly Ala Asn Leu
                165                 170                 175

Cys Ser Ser Phe Ser Ile Cys His Thr Phe Gln Trp His Glu Ala Met
                180                 185                 190

Phe Leu Leu Glu Phe Phe Leu Pro Leu Gly Ile Ile Leu Phe Cys Ser
                195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Arg Ile Arg Ile Phe Trp
                245                 250                 255

Leu Leu His Thr Ser Gly Thr Gln Asn Cys Glu Val Tyr Arg Ser Val
                260                 265                 270

Asp Leu Ala Phe Phe Ile Thr Leu Ser Phe Thr Tyr Met Asn Ser Met
    275                 280                 285

Leu Asp Pro Val Val Tyr Tyr Phe Ser Ser Pro Ser Phe Pro Asn Phe
290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
                340                 345                 350

Trp Ser Pro Ser Tyr Leu Gly Pro Thr Ser Pro
                355                 360
```

<210> SEQ ID NO 5
<211> LENGTH: 1041
<212> TYPE: DNA
<213> ORGANISM: Homo sapiens
<220> FEATURE:
<223> OTHER INFORMATION: human G-protein coupled receptor TGR183

<400> SEQUENCE: 5

```
atgtacaacg gtcgtgctg  ccgcatcgag  ggggacacca  tctcccaggt gatgccgccg    60
ctgctcattg tggcctttgt gctgggcgca ctaggcaatg gggtcgccct gtgtggtttc   120
tgcttccaca tgaagacctg gaagcccagc actgtttacc ttttcaattt ggccgtggct   180
gatttcctcc ttatgatctg cctgcctttt cggacagact attacctcag acgtagacac   240
```

-continued

```
tgggcttttg gggacattcc ctgccgagtg gggctcttca cgttggccat gaacagggcc      300
gggagcatcg tgttccttac ggtggtggct gcggacaggt atttcaaagt ggtccacccc      360
caccacgcgg tgaacactat ctccacccgg gtggcggctg gcatcgtctg caccctgtgg      420
gccctggtca tcctgggaac agtgtatctt ttgctgagga accatctctg cgtgcaagag      480
acggccgtct cctgtgagag cttcatcatg gagtcggcca atggctggca tgacatcatg      540
ttccagctgg agttctttat gccccctcggc atcatcttat tttgctcctt caagattgtt    600
tggagcctga ggcggaggca gcagctggcc agacaggctc ggatgaagaa ggcgacccgg      660
ttcatcatgg tggtggcaat tgtgttcatc acatgctacc tgcccagcgt gtctgctaga      720
ctctatttcc tctggacggt gccctcgagt gcctgcgatc cctctgtcca tgggccctg      780
cacataaccc tcagcttcac ctacatgaac agcatgctgg atcccctggt gtattatttt      840
tcaagcccct cctttcccaa attctacaac aagctcaaaa tctgcagtct gaaacccaag      900
cagccaggac actcaaaaac acaaaggccg gaagagatgc caattcgaa cctcggtcgc      960
aggagttgca tcagtgtggc aaatagtttc caaagccagt ctgatgggca tgggatccc      1020
cacattgttg agtggcactg a                                               1041
```

<210> SEQ ID NO 6
<211> LENGTH: 346
<212> TYPE: PRT
<213> ORGANISM: Homo sapiens
<220> FEATURE:
<223> OTHER INFORMATION: human G-protein coupled receptor TGR183

<400> SEQUENCE: 6

```
Met Tyr Asn Gly Ser Cys Cys Arg Ile Glu Gly Asp Thr Ile Ser Gln
  1               5                  10                  15

Val Met Pro Pro Leu Ile Val Ala Phe Val Leu Gly Ala Leu Gly
                 20                  25                  30

Asn Gly Val Ala Leu Cys Gly Phe Cys Phe His Met Lys Thr Trp Lys
             35                  40                  45

Pro Ser Thr Val Tyr Leu Phe Asn Leu Ala Val Ala Asp Phe Leu Leu
         50                  55                  60

Met Ile Cys Leu Pro Phe Arg Thr Asp Tyr Tyr Leu Arg Arg His
 65                  70                  75                  80

Trp Ala Phe Gly Asp Ile Pro Cys Arg Val Gly Leu Phe Thr Leu Ala
                 85                  90                  95

Met Asn Arg Ala Gly Ser Ile Val Phe Leu Thr Val Val Ala Ala Asp
            100                 105                 110

Arg Tyr Phe Lys Val Val His Pro His His Ala Val Asn Thr Ile Ser
            115                 120                 125

Thr Arg Val Ala Ala Gly Ile Val Cys Thr Leu Trp Ala Leu Val Ile
        130                 135                 140

Leu Gly Thr Val Tyr Leu Leu Leu Glu Asn His Leu Cys Val Gln Glu
145                 150                 155                 160

Thr Ala Val Ser Cys Glu Ser Phe Ile Met Glu Ser Ala Asn Gly Trp
                165                 170                 175

His Asp Ile Met Phe Gln Leu Glu Phe Phe Met Pro Leu Gly Ile Ile
            180                 185                 190

Leu Phe Cys Ser Phe Lys Ile Val Trp Ser Leu Arg Arg Arg Gln Gln
        195                 200                 205

Leu Ala Arg Gln Ala Arg Met Lys Lys Ala Thr Arg Phe Ile Met Val
    210                 215                 220
```

```
Val Ala Ile Val Phe Ile Thr Cys Tyr Leu Pro Ser Val Ser Ala Arg
225                 230                 235                 240

Leu Tyr Phe Leu Trp Thr Val Pro Ser Ser Ala Cys Asp Pro Ser Val
                245                 250                 255

His Gly Ala Leu His Ile Thr Leu Ser Phe Thr Tyr Met Asn Ser Met
                260                 265                 270

Leu Asp Pro Leu Val Tyr Tyr Phe Ser Pro Ser Phe Pro Lys Phe
                275                 280                 285

Tyr Asn Lys Leu Lys Ile Cys Ser Leu Lys Pro Lys Gln Pro Gly His
            290                 295                 300

Ser Lys Thr Gln Arg Pro Glu Glu Met Pro Ile Ser Asn Leu Gly Arg
305                 310                 315                 320

Arg Ser Cys Ile Ser Val Ala Asn Ser Phe Gln Ser Gln Ser Asp Gly
                325                 330                 335

Gln Trp Asp Pro His Ile Val Glu Trp His
                340                 345

<210> SEQ ID NO 7
<211> LENGTH: 1164
<212> TYPE: DNA
<213> ORGANISM: Homo sapiens
<220> FEATURE:
<223> OTHER INFORMATION: human G-protein coupled receptor TGR4a allele 2

<400> SEQUENCE: 7
atgaatcggc accatctgca ggatcacttt ctggaaatag acaagaagaa ctgctgtgtg      60
ttccgagatg acttcattgc caaggtgttg ccgccggtgt tggggctgga gtttatcttt     120
gggcttctgg gcaatggcct tgccctgtgg attttctgtt ccacctcaa gtcctggaaa      180
tccagccgga ttttcctgtt caacctggca gtagctgact tctactgat catctgcctg      240
ccgttcgtga tggactacta tgtgcggcgt tcagactgga gtttggggga catcccttgc     300
cggctggtgc tcttcatgtt tgccatgaac cgccagggca gcatcatctt cctcacggtg     360
gtggcggtag acaggtattt ccgggtggtc catccccacc acgccctgaa caagatctcc     420
aattggacag cagccatcat ctcttgcctt ctgtgggca tcactgttgg cctaacagtc      480
cacctcctga agaagaagtt gctgatccag aatggccctg caaatgtgtg catcagcttc     540
agcatctgcc ataccttccg gtggcacgaa gctatgttcc tcctggagtt cctcctgccc     600
ctgggcatca tcctgttctg ctcagccaga attatctgga gctgcggca gagacaaatg     660
gaccggcatg ccaagatcaa gagagccatc accttcatca tggtggtggc catcgtcttt     720
gtcatctgct tccttcccag cgtggttgtg cggatccgca tcttctggct cctgcacact     780
tcgggcacgc agaattgtga agtgtaccgc tcggtggacc tggcgttctt tatcactctc     840
agcttcacct acatgaacag catgctggac cccgtggtgt actacttctc agcccatcc     900
tttcccaact tcttctccac tttgatcaac cgctgcctcc agaggaagat gacaggtgag     960
ccagataata accgcagcac gagcgtcgag ctcacagggg accccaacaa accagaggc    1020
gctccagagg cgttaatggc caactccggt gagccatgga gcccctctta tctgggccca    1080
acctcaaata accattccaa gaagggacat tgtcaccaag aaccagcatc tctggagaaa    1140
cagttgggct gttgcatcga gtaa                                           1164

<210> SEQ ID NO 8
<211> LENGTH: 387
<212> TYPE: PRT
```

-continued

<213> ORGANISM: Homo sapiens
<220> FEATURE:
<223> OTHER INFORMATION: human G-protein coupled receptor TGR4a allele 2

<400> SEQUENCE: 8

```
Met Asn Arg His His Leu Gln Asp His Phe Leu Glu Ile Asp Lys Lys
 1               5                  10                  15

Asn Cys Cys Val Phe Arg Asp Asp Phe Ile Ala Lys Val Leu Pro Pro
                20                  25                  30

Val Leu Gly Leu Glu Phe Ile Phe Gly Leu Leu Gly Asn Gly Leu Ala
            35                  40                  45

Leu Trp Ile Phe Cys Phe His Leu Lys Ser Trp Lys Ser Ser Arg Ile
 50                  55                  60

Phe Leu Phe Asn Leu Ala Val Ala Asp Phe Leu Leu Ile Ile Cys Leu
 65                  70                  75                  80

Pro Phe Val Met Asp Tyr Tyr Val Arg Arg Ser Asp Trp Lys Phe Gly
                85                  90                  95

Asp Ile Pro Cys Arg Leu Val Leu Phe Met Phe Ala Met Asn Arg Gln
               100                 105                 110

Gly Ser Ile Ile Phe Leu Thr Val Ala Val Asp Arg Tyr Phe Arg
            115                 120                 125

Val Val His Pro His His Ala Leu Asn Lys Ile Ser Asn Trp Thr Ala
130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
210                 215                 220

Lys Ile Lys Arg Ala Ile Thr Phe Ile Met Val Val Ala Ile Val Phe
225                 230                 235                 240

Val Ile Cys Phe Leu Pro Ser Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
370                 375                 380

Cys Ile Glu
```

<210> SEQ ID NO 9
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 9

Gly Gly Gly Gly Gly Gly Gly Gly Gly Gly Gly Gly Gly Gly Gly Gly
 1               5                  10                  15
Gly Gly Gly Gly Gly Gly Gly Gly Gly Gly Gly Gly Gly Gly Gly Gly
             20                  25                  30
Gly Gly Gly Gly Gly Gly Gly Gly Gly Gly Gly Gly Gly Gly Gly Gly
         35                  40                  45
Gly Gly Gly Gly Gly Gly Gly Gly Gly Gly Gly Gly Gly Gly Gly Gly
     50                  55                  60
Gly Gly Gly Gly Gly Gly Gly Gly Gly Gly Gly Gly Gly Gly Gly Gly
 65                  70                  75                  80
Gly Gly Gly Gly Gly Gly Gly Gly Gly Gly Gly Gly Gly Gly Gly Gly
                 85                  90                  95
Gly Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly Gly
            180                 185                 190
Gly Gly Gly Gly Gly Gly Gly Gly
        195                 200

RECEPTOR LIGANDS AND METHODS OF MODULATING RECEPTORS

CROSS REFERENCE TO RELATED APPLICATIONS

This application claims benefit of U.S. Provisional Application No. 60/421,142, filed Nov. 25, 2002, and U.S. Provisional Application No. 60/444,153, filed Jan. 30, 2003, each of which is herein incorporated by reference.

FIELD OF THE INVENTION

This invention relates to the identification of specific ligands that bind previously identified G-protein coupled receptors (GPCRs) and methods for identifying and using modulators of the receptor-ligand interactions for various therapeutic indications.

BACKGROUND OF THE INVENTION

G-protein coupled receptors are cell surface receptors that indirectly transduce extracellular signals to downstream effectors, e.g., intracellular signaling proteins, enzymes, or channels. Changes in the activity of these effectors then mediate subsequent cellular events. The interaction between the receptor and the downstream effector is mediated by a G-protein, a heterotrimeric protein that binds GTP. Examples of mammalian G proteins include Gi, Go, Gq, Gs, and Gt (for a review, see, e.g., Morris and Malbon, *Physiol. Reviews* 79: 1373–1430; 1999).

G-protein coupled receptors ("GPCRs") typically have seven transmembrane regions, along with an extracellular domain and a cytoplasmic tail at the C-terminus. These receptors form a large superfamily of related receptor molecules that play a key role in many signaling processes, such as sensory and hormonal signal transduction. The further identification of GPCRs and the natural ligands of the receptors is important for understanding the normal process of signal transduction as well as theirs involvement in pathologic processes. For example, GPCRs can be used for disease diagnosis as well as for drug discovery. GPCR ligands may be used for the treatment of GPCR-related disorders and for the identification of additional modulators of GPCR activity. Further identification of GPCRs and ligands that bind to GPCRs is therefore of great interest.

Nicotinic acid (vitamin B3, also known as Niacin) is an essential dietary ingredient, its deficiency causes pellagra in humans. It is incorporated into either of two coenzymes, nicotinamide adenine dinucleotide (NAD) or nicotinamide adenine dinucleotide phosphate (NADP). Many biochemical reactions in glucose, lipid and protein metabolism are dependent on these coenzymes.

Nicotinic acid, at gram dose, has also been used as a drug for the treatment of hyperlipidemia, e.g., acipimox. It is effective in reducing total cholesterol (TC), low-density lipoprotein cholesterol (LDL-C), triglycerides (TG) and lipoprotein (a) [Lp(a)]. At the same time, it also increases high-density lipoprotein cholesterol (HDL-C). Because epidemiological studies have established that the risk of coronary heart disease is linked positively to the levels of TC and LDL-C, and inversely to the level of HDL-C, the effects of nicotinic acid are highly desirable. Recent clinical studies also indicate that a combination of nicotinic acid therapy with statins has added benefit.

The mechanism by which nicotinic acid alters lipid profiles has not been well defined. It may involve several actions including inhibition of lipolysis in adipocytes, inhibition of release of free fatty acids from adipose tissue, and increase of lipoprotein lipase activity. The action of nicotinic acid on adipocytes may be mediated by inhibition of adenylyl cyclase through pertussis toxin-sensitive G proteins. A binding site for nicotinic acid in adipose tissues was recently described, but not yet characterized on molecular level. The most prominent side effects of nicotinic acid are skin flushing and itching on the face and neck. This "niacin flush" can be very uncomfortable, and greatly limits its use. Although not fully proved, it is proposed that the side effect of skin flush is mediated by vasodilating prostaglandin D2 released from macrophages surrounding cutaneous blood vessels. Supporting this proposal, a binding site for nicotinic acid has been detected in mouse macrophages.

Nicotinic acid derivatives are also used as vasodilators to treat peripheral vascular disease and other disorders of circulation, including Raynaud's syndrome. They can reduce concentrations of fibrinogen and lower blood viscosity (the fluidity of the blood).

Without knowing its molecular target(s), it is almost impossible to improve the potency, efficacy and specificity of nicotinic acid in order to obtain a superior medicine with better therapeutic and side effect profiles. The current invention is based on the discovery that nicotinic acid is a ligand for two GPCRs.

BRIEF SUMMARY OF THE INVENTION

The present invention relates to the identification and characterization of ligands for particular G protein-coupled receptors (GPCRs) and methods for identifying and using modulators of the receptor-ligand interactions. Specifically, the inventors have shown that a natural ligand for TGR4, e.g., SEQ ID NO:4, and TGR183, e.g., SEQ ID NO:6, is nicotinic acid. Modulators of the receptor-ligand interaction may be used, for example, for the treatment of a disease or condition associated with a TGR4 or TGR183, e.g., hyperlipidemia.

In one aspect, the invention provides a method of identifying a modulator of a TGR4 polypeptide that has G-protein coupled receptor activity and (A) comprises at least 70% amino acid sequence identity to SEQ ID NO:4, (B) comprises at least 50 contiguous amino acids of SEQ ID NO:4, or (C) comprises the amino acid sequence of SEQ ID NO:4; wherein the method comprises: contacting a compound with the polypeptide; and determining the level of activation of the polypeptide by nicotinic acid in comparison to the level of activity in the absence of the compound. In some embodiments, the TGR4 polypeptide consists of at least 50, often at least 40, 30, or 20, contiguous amino acids of SEQ ID NO:4. Often, the TGR4 is recombinant. In some embodiments, the step of determining the level of activity comprises determining the level of binding of the modulator, or the natural ligand, e.g., nicotinic acid, to the TGR4. In other embodiments, the method may comprise detecting an alteration in nicotinic acid-induced changes in TGR4 activity, e.g., increases in intracellular calcium or inositol phosphate accumulation, or a decrease in intracellular cAMP concentration.

In another aspect, the invention provides a method of identifying a modulator of a TGR183 polypeptide that has G-protein coupled receptor activity and (A) comprises at least 70% amino acid sequence identity to SEQ ID NO:6, (B) comprises at least 50 contiguous amino acids of SEQ ID NO:6, or (C) comprises the amino acid sequence of SEQ ID NO:6; wherein the method comprises: contacting a compound with the polypeptide; and determining the level of activation of the polypeptide by nicotinic acid in comparison to the level of activation in the absence of the compound. In some embodiments, the TGR183 polypeptide consists of at least 50, often at least 40, 30 or 20, contiguous amino acids of SEQ ID NO:6. Often, the TGR183 is recombinant. In some embodiments, the step of determining the level of activity may comprise determining the level of binding of the modulator, or the natural ligand, to the TGR183. In other embodiments, the method may comprise detecting an alteration in nicotinic acid-induced TGR183 activity, e.g., increases in intracellular calcium or inositol phosphate accumulation or a decrease in intracellular cAMP concentration.

In another embodiment, the invention provides a method of treating a patient with a TGR4 or TGR183-associated disorder, the method comprising administering a therapeutically effective amount of a compound identified as set forth above. The disorder may be, but is not limited to, a disorder involving lipid metabolism including, hyperlipidemia, atherosclerosis, coronary artery disease, diabetes, stroke, and obesity; or a disorder associated with the vasodilation effect of nicotinic acid on the coronary and/or peripheral vasculature. The disorder may be one in which the anti-lipolysis effect of nicotinic acid can be beneficial, such as cachexia associated with cancer. In some embodiments, the compound may modulate a nicotinic acid-induced TGR4 or TGR183-induced activity, but not binding of nicotinic acid to TGR4 or TGR183. An exemplary compound is an antibody. In some embodiments, the compound may be an agonist, e.g., for treating hyperlipidemia.

In other aspects, the invention provides a method of treating a patient with an inflammatory disease, typically using a compound that modulates TGR4 activity. The compound may modulate TGR4-induced activity, but not nicotinic acid binding to TGR4. In some embodiments, the compounds may be an antagonist, e.g., for treating an inflammatory response such as that resulting from a chronic disease or injury.

BRIEF DESCRIPTION OF THE DRAWINGS

FIG. 1 shows the alignment of TGR4a (SEQ ID NO:2) (also referred to as HM74) and TGR183 (SEQ ID NO:6).

FIG. 5 shows the expression pattern of TGR183 in human and mouse adipocytes.

FIG. 6 shows the expression pattern of TGR4 in human and mouse adipocytes.

FIG. 8 shows the expression patterns of TGR4 in various tissues compared to the expression of TGR183.

DETAILED DESCRIPTION OF THE INVENTION

Introduction

Figure 2:
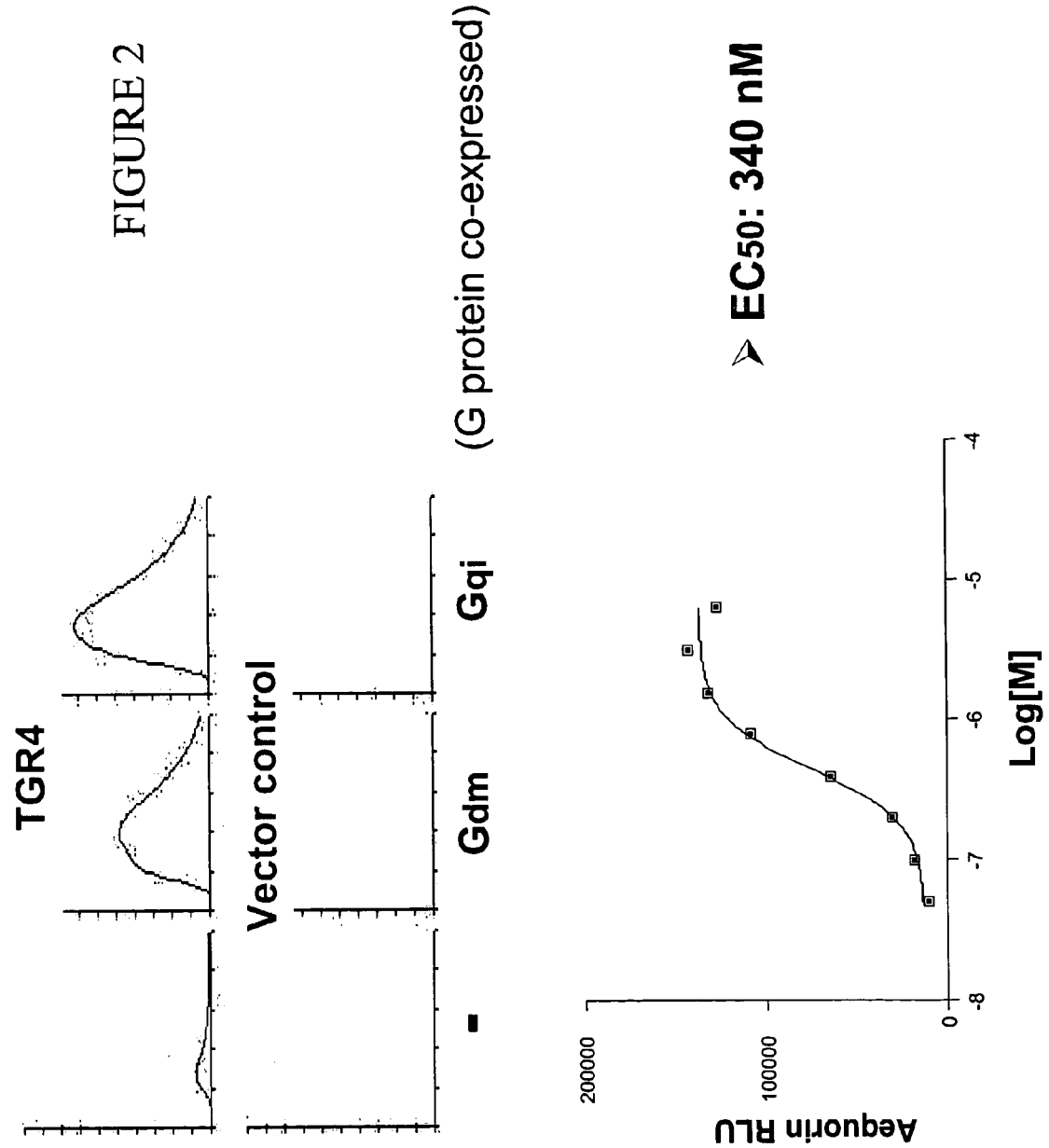
FIG. 2 depicts the results of an Aequorin assay showing that nicotinic acid activates TGR4.

The current invention is based on the discovery that nicotinic acid is a natural ligand for TGR4, e.g., SEQ ID NO:4 and TGR183, e.g., SEQ ID NO:6. Accordingly, nicotinic acid or analogs, conservative modifications, or variants thereof, may be used to modulate TGR4 or TGR183 activity and for the treatment of diseases or conditions associated with these GPCRs. Further, nicotinic acid may be used to identify compounds that modulate ligand binding and activation of the cognate GPCR. Such modulators may be used to treat TGR4 and TGR183-related disorders.

Nicotinic acid (vitamin B3, also known as niacin) is an essential dietary ingredient, for example, its deficiency causes pellagra in humans. It is incorporated into either of two coenzymes, nicotinamide adenine dinucleotide (NAD) or nicotinamide adenine dinucleotide phosphate (NADP). Many biochemical reactions in glucose, lipid and protein metabolism are dependent on these coenzymes.

Nicotinic acid has also been used as a drug for the treatment of hyperlipidemia. It is effective in reducing total cholesterol (TC), low-density lipoprotein cholesterol (LDL-C), triglycerides (TG) and lipoprotein (a) [Lp(a)]. At the same time, it also increases high-density lipoprotein cholesterol (HDL-C).

The present invention thus provides nucleic acids encoding G protein coupled receptors TGR4 and TGR183; and natural ligands of these GPCRs. TGR4 is about 50% identical to TGR183 (see, e.g., the alignment provided in FIG. 1). The GPCR nucleic acid and protein sequences provide means for assaying for and for identifying modulators of ligand binding and ligand-mediated GPCR signal transduction, e.g., activators, inhibitors, stimulators, enhancers, agonists, and antagonists. Such modulators are useful for pharmacological modulation of signaling pathways, e.g., in cells and tissues that express TGR4 or TGR183.

Exemplary TGR4 nucleic acid and protein sequences have been described, see, e.g., WO 98/56820, WO 02/13845, WO 00/22129, WO 01/36471, WO 02/18938, and WO 01/94629. Additionally, exemplary TGR183 nucleic acid and protein sequences have been described (see, e.g., WO 01/74904; WO 02/06466; US 2002052022; WO 01/87937; WO 01/73029; WO 01/77320; WO 01/36473; WO 01/36471; WO 01/98330; and WO 02/18579).

The GPCR ligands identified herein and modulators of ligand binding and GPCR activity can also be used to further study signal transduction. Thus, the invention provides assays for signal transduction modulation, where the GPCRs act as direct or indirect reporter molecules for the effect of modulators on ligand-mediated signal transduction. GPCRs can be used in assays in vitro, ex vivo, and in vivo, e.g., to measure changes in transcriptional activation of GPCRs; ligand binding; phosphorylation and dephosphorylation; GPCR binding to G-proteins; G-protein activation; regulatory molecule binding; voltage, membrane potential, and conductance changes; ion flux; changes in intracellular second messengers such as cAMP, diacylglycerol, and inositol triphosphate; and changes in intracellular calcium levels.

Methods of assaying for modulators of ligand binding and signal transduction include in vitro ligand binding assays using the GPCRs, portions thereof such as the extracellular domain, or chimeric proteins comprising one or more domains of a GPCR, oocyte GPCR expression or tissue culture cell GPCR expression, either naturally occurring or recombinant; membrane expression of a GPCR, either naturally occurring or recombinant; tissue expression of a GPCR; expression of a GPCR in a transgenic animal, etc.

Related GPCR genes, e.g., from other species should share at least about 70%, 80%, 90%, or greater, amino acid identity over a amino acid region at least about 25 amino acids in length, optionally 50 to 100 amino acids in length.

Specific regions of the GPCR nucleotide and amino acid sequences may be used to identify polymorphic variants, interspecies homologs, and alleles of GPCRs. This identification can be made in vitro, e.g., under stringent hybridization conditions or PCR (using primers that hybridize to SEQ ID NO:1, SEQ ID NO:3, SEQ ID NO:7, or SEQ ID NO:5), and sequencing, or by using the sequence information in a computer system for comparison with other nucleotide sequences. Typically, identification of polymorphic variants and alleles of a GPCR is made by comparing an amino acid sequence of about 25 amino acids or more, e.g., 50–100 amino acids. Amino acid identity of approximately at least 70% or above, optionally 75%, 80%, 85% or 90–95% or above typically demonstrates that a protein is a polymorphic variant, interspecies homolog, or allele of a GPCR. Sequence comparison is performed using the BLAST and BLAST 2.0 sequence comparison algorithms with default parameters, discussed below. Antibodies that bind specifically to a GPCR or a conserved region thereof can also be used to identify alleles, interspecies homologs, and polymorphic variants. The polymorphic variants, alleles and interspecies homologs are expected to retain the seven transmembrane structure of a G-protein coupled receptor.

Definitions

The term "nicotinic acid" or "niacin" as used herein refers to 3-pyridinecarboxylic acid. The term encompasses related heterocyle compounds and derivatives, and their salts, including pyridazine-4-carboxylic acid, inositol nicotinate; 5-methylpyrazine-2-carboxylic acid-4-oxide (acipimox), nicotinyl alcohol, and nicotinic acid esters that activate TGR4 or TGR183.

"GPCR," "TGR", "TGR4", or "TGR183" all refer to G-protein coupled receptors, the genes for most of which have been mapped to particular chromosomes and which are expressed in particular cell types. These GPCRs have seven transmembrane regions and have "G-protein coupled receptor activity," e.g., they bind to G-proteins in response to extracellular stimuli and promote production of second messengers such as diacylglycerol (DAG), IP$_3$, cAMP, and Ca$^{2+}$ via stimulation of downstream effectors such as phospholipase C and adenylate cyclase (for a description of the structure and function of GPCRs, see, e.g., Fong, supra, and Baldwin, supra).

Topologically, GPCRs have an N-terminal "extracellular domain," a "transmembrane domain" comprising seven transmembrane regions and corresponding cytoplasmic and extracellular loops, and a C-terminal "cytoplasmic domain" (see, e.g., Buck & Axel, *Cell* 65:175–187 (1991)). These domains can be structurally identified using methods known to those of skill in the art, such as sequence analysis programs that identify hydrophobic and hydrophilic domains (see, e.g., Kyte & Doolittle, *J. Mol. Biol.* 157: 105–132 (1982)). Such domains are useful for making chimeric proteins and for in vitro assays of the invention.

The terms "GPCR" and "TGR4", or "TGR183" therefore refer to nucleic acid and polypeptide polymorphic variants, alleles, mutants, and interspecies homologs and GPCR domains thereof that: (1) have an amino acid sequence that has greater than about 65% amino acid sequence identity, 70%, 75%, 80%, 85%, 90%, preferably 91%, 92%, 93%, 94%, 95%, 96%, 97%, 98% or 99% or greater amino acid sequence identity, preferably over a window of at least about 25, 50, 100, 200, 500, 1000, or more amino acids, to a sequence of SEQ ID NO:2, SEQ ID NO:4, SEQ ID NO:8, or SEQ ID NO:6; (2) bind to antibodies raised against an immunogen comprising an amino acid sequence of SEQ ID NO:2, SEQ ID NO:4 or SEQ ID NO:6 and conservatively modified variants thereof; (3) have at least 15 contiguous amino acids, more often, at least 20, 30, 40, 50 or 100 contiguous amino acids, of SEQ ID NO:2, SEQ ID NO:4, SEQ ID NO:8, or SEQ ID NO:6; (4) specifically hybridize (with a size of at least about 100, preferably at least about 500 or 1000 nucleotides) under stringent hybridization conditions to a sequence of SEQ ID NO:1, SEQ ID NO:3, SEQ ID NO:7, SEQ ID NO:7, or SEQ ID NO:5 and conservatively modified variants thereof; (5) have a nucleic acid sequence that has greater than about 95%, preferably greater than about 96%, 97%, 98%, 99%, or higher nucleotide sequence identity, preferably over a region of at least about 50, 100, 200, 500, 1000, or more nucleotides, to SEQ ID NO:1, SEQ ID NO:3, SEQ ID NO:7, or SEQ ID NO:5; or (6) are amplified by primers that specifically hybridize under stringent conditions to SEQ ID NO:1, SEQ ID NO:3, SEQ ID NO:7, or SEQ ID NO:5. This term also refers to a domain of a GPCR, as described above, or a fusion protein comprising a domain of a GPCR linked to a heterologous protein. A GPCR polynucleotide or polypeptide sequence of the invention is typically from a mammal including, but not limited to, human, mouse, rat, hamster, cow, pig, horse, sheep, or any mammal. A "TGR4 or TGR183 polynucleotide" and a "TGR4 or TGR183 polypeptide," are both either naturally occurring or recombinant.

A "full length" TGR4 or TGR183 protein or nucleic acid refers to a polypeptide or polynucleotide sequence, or a variant thereof, that contains all of the elements normally contained in one or more naturally occurring, wild type TGR4 or TGR183 polynucleotide or polypeptide sequences. It will be recognized, however, that derivatives, homologs, and fragments of TGR4 or TGR183 can be readily used in the present invention.

In some embodiments, the GPCR used in the methods of the invention is a fragment or domain that essentially consists of, at least 15, often at least 20, 30, 40, or 50, contiguous amino acids of SEQ ID NO:2, SEQ ID NO:4, SEQ ID NO:8, or SEQ ID NO:6.

"Extracellular domain" refers to the domain of a GPCR that protrudes from the cellular membrane and often binds to an extracellular ligand. This domain is often useful for in vitro ligand binding assays, both soluble and solid phase.

"Transmembrane domain" comprises seven transmembrane regions plus the corresponding cytoplasmic and extracellular loops. Certain regions of the transmembrane domain can also be involved in ligand binding.

"Cytoplasmic domain" refers to the domain of a GPCR that protrudes into the cytoplasm after the seventh transmembrane region and continues to the C-terminus of the polypeptide.

"GPCR activity" refers to the ability of a GPCR to transduce a signal. Such activity can be measured, e.g., in a heterologous cell, by coupling a GPCR (or a chimeric GPCR) to a G-protein and a downstream effector such as PLC or adenylate cyclase, and measuring increases in intracellular calcium (see, e.g., Offermans & Simon, *J. Biol. Chem.* 270:15175–15180 (1995)). Receptor activity can be effectively measured by recording ligand-induced changes in $[Ca^{2+}]_i$ using fluorescent Ca$^{2+}$-indicator dyes and fluorometric imaging. A "natural ligand-induced activity" as used herein, refers to activation of the GPCR by a natural ligand of the GPCR. Activity can be assessed using any number of endpoints to measure the GPCR activity. For example, activity of a a TGR4 or TGR183, may be assessed using an assay such as calcium mobilization, e.g., an Aequorin luminescence assay.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like.

"Biological sample" as used herein is a sample of biological tissue or fluid that contains GPCR nucleic acids or polypeptides. Such samples include, but are not limited to, tissue isolated from humans, mice, and rats. Biological samples may also include sections of tissues such as frozen sections taken for histologic purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues typically depend on the known expression profile of the GPCR, and include e.g., adipose, leukocytes, neutrophils, monocytes, bone marrow, and spleen.

The phrase "functional effects" in the context of assays for testing compounds that modulate GPCR-mediated signal transduction includes the determination of any parameter that is indirectly or directly under the influence of a GPCR, e.g., a functional, physical, or chemical effect. It includes ligand binding, changes in ion flux, membrane potential, current flow, transcription, G-protein binding, gene amplification, expression in cancer cells, GPCR. phosphorylation or dephosphorylation, signal transduction, receptor-ligand interactions, second messenger concentrations (e.g., cAMP, cGMP, $IP_3$, DAG, or intracellular $Ca^{2+}$), in vitro, in vivo, and ex vivo and also includes other physiologic effects such as increases or decreases of neurotransmitter or hormone release; or increases in the synthesis of particular compounds, e.g., triglycerides.

By "determining the functional effect" is meant assaying for a compound that increases or decreases a parameter that is indirectly or directly under the influence of a GPCR, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of GPCRs; ligand binding assays; voltage, membrane potential and conductance changes; ion flux assays; changes in intracellular second messengers such as cAMP and inositol triphosphate ($IP_3$); changes in intracellular calcium levels; neurotransmitter release, and the like.

"Inhibitors," "activators," and "modulators" of GPCRs are used interchangeably to refer to inhibitory, activating, or modulating molecules identified using in vitro and in vivo assays for signal transduction, e.g., ligands, agonists, antagonists, and their homologs and mimetics. Such modulating molecules, also referred to herein as compounds, include polypeptides, antibodies, amino acids, nucleotides, lipids, carbohydrates, or any organic or inorganic molecule. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Modulators include compounds that, e.g., alter the interaction of a polypeptide with: extracellular proteins that bind activators or inhibitors; G-proteins; G-protein alpha, beta, and gamma subunits; and kinases. Modulators also include genetically modified versions of GPCRs, e.g., with altered activity, as well as naturally occurring and synthetic ligands, antagonists, agonists, antibodies, small chemical molecules and the like. Such assays for inhibitors and activators include, e.g., expressing GPCRs in vitro, in cells or cell membranes, applying putative modulator compounds, and then determining the functional effects on signal transduction, as described above.

Samples or assays comprising GPCRs that are treated with a potential activator, inhibitor, or modulator are compared to control samples without the inhibitor, activator, or modulator to examine the extent of inhibition. Control samples (untreated with inhibitors) are assigned a relative GPCR activity value of 100%. Inhibition of a GPCR is achieved when the GPCR activity value relative to the control is about 80%, preferably 50%, more preferably 25–0%. Activation of a GPCR is achieved when the GPCR activity value relative to the control (untreated with activators) is 110%, more preferably 150%, more preferably 200–500% (i.e., two to five fold higher relative to the control), more preferably 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated GPCR nucleic acid is separated from open reading frames that flank the GPCR gene and encode proteins other than the GPCR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Biologically active" GPCR refers to a GPCR having signal transduction activity and G protein coupled receptor activity, as described above.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1994–1999).

A preferred example of algorithms that are suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec –2 min., an annealing phase lasting 30 sec. –2 min., and an extension phase of about 72° C. for 1–2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)$'_2$, a dimer of Fab which itself is a light chain joined to $V_H$-$C_H$1 by a disulfide bond. The F(ab)$'_2$ may be reduced under mild conditions to break the disulfide linkage in the hinge region, thereby converting the F(ab)$'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-GPCR" antibody is an antibody or antibody fragment that specifically binds a polypeptide encoded by a GPCR gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a particular GPCR can be selected to obtain only those polyclonal antibodies that are specifically immunoreactive with the GPCR, and not with other proteins, except for polymorphic variants, orthologs, and alleles of the GPCR. This selection may be achieved by subtracting out antibodies that cross-react with GPCR molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background. Antibodies that react only with a particular GPCR ortholog, e.g., from specific species such as rat, mouse, or human, can also be made as described above, by subtracting out antibodies that bind to the same GPCR from another species.

The phrase "selectively associates with" refers to the ability of a nucleic acid to "selectively hybridize" with another as defined above, or the ability of an antibody to "selectively (or specifically) bind" to a protein, as defined above.

Isolation of Nucleic Acids Encoding GPCRs

A. General Recombinant DNA Methods

This invention relies on routine techniques in the field of recombinant genetics. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994–1999). Methods that are used to produce GPCRs for use in the invention may also be employed to produce protein ligands or polypeptides that modulate ligand binding to the receptor, for use in the invention.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

B. Cloning Methods for the Isolation of Nucleotide Sequences Encoding GPCRs

In general, the nucleic acid sequences encoding GPCRs and related nucleic acid sequence homologs are cloned from cDNA and genomic DNA libraries by hybridization with a probe, or isolated using amplification techniques with oligonucleotide primers, and verified by sequencing. For example, GPCR sequences are typically isolated from mammalian nucleic acid (genomic or cDNA) libraries by hybridizing with a nucleic acid probe, the sequence of which can be derived from SEQ ID NO:1, SEQ ID NO:3, SEQ ID NO:7, or SEQ ID NO:5. Suitable tissues from which GPCR RNA and cDNA can be isolated include, e.g., neural tissue, e.g., peripheral neural tissue and brain; immune cells and tissues, e.g., spleen, lymphocytes, bone marrow, and the like; adipose tissue; bone tissue; and other tissues.

Amplification techniques using primers can also be used to amplify and isolate GPCR nucleic acids from DNA or RNA. Suitable primers can be designed using criteria well known in the art (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length GPCRs.

Nucleic acids encoding GPCRs can also be isolated from expression libraries using antibodies as probes. Such polyclonal or monoclonal antibodies can be raised using the sequence of SEQ ID NO:2, SEQ ID NO:4, SEQ ID NO:8, or SEQ ID NO:6.

GPCR polymorphic variants, alleles, and interspecies homologs that are substantially identical to a GPCR can be isolated using GPCR nucleic acid probes, and oligonucleotides under stringent hybridization conditions, by screening libraries. Alternatively, expression libraries can be used to clone GPCRs and GPCR polymorphic variants, alleles, and interspecies homologs, by detecting expressed homologs immunologically with antisera or purified antibodies made against GPCRs, which also recognize and selectively bind to the GPCR homolog. Methods of constructing cDNA and genomic libraries are well known in the art (see, e.g., Sambrook & Russell, supra; and Ausubel et al., supra).

An alternative method of isolating GPCR nucleic acids and their homologs combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of GPCRs directly from mRNA, from cDNA, from genomic libraries or cDNA libraries. Degenerate oligonucleotides can be designed to amplify GPCR homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of GPCR-encoding mRNA in physiological samples, for nucleic acid sequencing, or for other purposes. Genes amplified by the PCR reaction can be purified from agarose gels and cloned into an appropriate vector.

Gene expression can also be analyzed by techniques known in the art, e.g., reverse transcription and amplification of mRNA, isolation of total RNA or poly A$^+$ RNA, northern blotting, dot blotting, in situ hybridization, RNase protection, probing DNA microchip arrays, and the like. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

Synthetic oligonucleotides can be used to construct recombinant GPCR genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the GPCR nucleic acid. The specific subsequence is then ligated into an expression vector.

The nucleic acid encoding a GPCR is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising GPCRs or domains thereof can be made according to standard techniques. For example, a domain such as ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, luciferase, or β-gal.

C. Expression in Prokaryotes and Eukaryotes

To obtain high level expression of a cloned gene or nucleic acid, such as cDNAs encoding GPCRs, or a protein ligand, one typically subclones a nucleic acid sequence encoding the protein of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook & Russell and Ausubel et al. Bacterial expression systems for expressing the protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the GPCR encoding nucleic acid in host cells. A typical expression cassette thus contains a promoter operably linked to the nucleic acid sequence encoding a GPCR and signals required for efficient polyadenylation of the transcript, ribosome binding sites, and translation termination. The nucleic acid sequence encoding a GPCR may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of GPCR protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Russell & Sambrook, supra). It is only necessary that the particular genetic engineering procedure used be capable of successfully introducing at least one gene into the host cell capable of expressing a GPCR.

After the expression vector is introduced into the cells, the transfected cells are cultured under conditions favoring expression of a GPCR, which is recovered from the culture using standard techniques identified below.

Transgenic animals, including knockout transgenic animals, that include additional copies of a GPCR and/or altered or mutated GPCR transgenes can also be generated. A "transgenic animal" refers to any animal (e.g. mouse, rat, pig, bird, or an amphibian), preferably a non-human mammal, in which one or more cells contain heterologous nucleic acid introduced using transgenic techniques well known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

In other embodiments, transgenic animals are produced in which expression of a GPCR is silenced. Gene knockout by homologous recombination is a method that is commonly used to generate transgenic animals. Transgenic mice can be derived using methodology known to those of skill in the art, see, e.g., Hogan et al., *Manipulating the Mouse Embryo: A Laboratory Manual*, (1988); *Teratocarcinomas and Embryonic Stem Cells: A Practical Approach*, Robertson, ed., (1987); and Capecchi et al., *Science* 244:1288 (1989).

Purification of GPCRs

Either naturally occurring or recombinant GPCRs can be purified for use in functional assays. Optionally, recombinant GPCRs are purified. Naturally occurring GPCRs are purified, e.g., from any suitable tissue or cell expressing naturally occurring GPCRs. Recombinant GPCRs are purified from any suitable bacterial or eukaryotic expression system, e.g., CHO cells or insect cells.

A GPCR may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Russell & Sambrook, supra).

A number of procedures can be employed when a recombinant GPCR is being purified. For example, proteins having established molecular adhesion properties can be reversibly fused to a GPCR. With the appropriate ligand, a GPCR can be selectively adsorbed to a purification column and then freed from the column in a relatively pure form. The fused protein is then removed by enzymatic activity. Finally, a GPCR could be purified using immunoaffinity columns.

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein using techniques known in the art (see, e.g., Russell & Sambrook, supra; and Ausubel et al., supra).

Immunological Detection of GPCRs

In addition to the detection of GPCR genes and gene expression using nucleic acid hybridization technology, one can also use antibodies to detect or modulate GPCRs that are used in the invention. A general overview of the applicable technology can be found in Harlow & Lane, *Antibodies: A Laboratory Manual* (1988) and Harlow & Lane, *Using Antibodies* (1999). Again, these methods are also applicable to the preparation and use of antibodies that specifically bind to other molecules used in the invention, e.g., peptide ligands.

Methods of producing polyclonal and monoclonal antibodies that react specifically with GPCRs are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Such antibodies can be used for therapeutic and diagnostic applications, e.g., in the treatment and/or detection of any of the GPCR-associated diseases or conditions described herein.

A number of GPCRs comprising immunogens may be used to produce antibodies specifically reactive with GPCRs. For example, a recombinant GPCR or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Typically, polyclonal antisera with a titer of $10^4$ or greater are selected and tested for their cross reactivity against non-GPCR proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once GPCR specific antibodies are available, GPCRs can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

GPCRs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the GPCR or antigenic subsequence thereof).

Immunoassays also often use a labeling agent to specifically bind to and label the complex formed by the antibody and antigen. The labeling agent may itself be one of the moieties comprising the antibody/antigen complex. Thus, the labeling agent may be a labeled GPCR polypeptide or a labeled anti-GPCR antibody. Alternatively, the labeling agent may be a third moiety, such as a secondary antibody, that specifically binds to the antibody/GPCR complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111: 1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of GPCR present in the sample is measured indirectly by measuring the amount of a known, added (exogenous) GPCR displaced (competed away) from an anti-GPCR antibody by the unknown GPCR present in a sample. Commonly used assay formats include Western blots (immunoblots), which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize GPCRs, or secondary antibodies that recognize anti-GPCR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3- dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cross-Reactivity Determinations

Immunoassays in the competitive binding format can also be used for cross-reactivity determinations. For example, a protein at least partially encoded by SEQ ID NO:1, SEQ ID NO:3, SEQ ID NO:7, or SEQ ID NO:5 can be immobilized to a solid support. Proteins (e.g., GPCR proteins and homologs) are added to the assay that compete for binding of the antisera to the immobilized antigen. The ability of the added proteins to compete for binding of the antisera to the immobilized protein is compared to the ability of GPCRs encoded by SEQ ID NO:1, SEQ ID NO:3, SEQ ID NO:7, or SEQ ID NO:5 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a GPCR, to the immunogen protein (i.e., the GPCR of SEQ ID NO:2, SEQ ID NO:4, SEQ ID NO:8, or SEQ ID NO:6). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:1, SEQ ID NO:3, SEQ ID NO:7 or SEQ ID NO:5 that is required to inhibit 50% of binding, then the second protein is said to specifically bind to the polyclonal antibodies generated to a GPCR immunogen.

Assays for Modulators of GPCRs

A. Assays for GPCR Activity

TGR4 and TGR183 and their alleles and polymorphic variants are G-protein coupled receptors that participate in signal transduction and are associated with cellular function in a variety of cells, e.g., adipocytes and immune system cells, e.g., spleen cells, bone marrow, and leukocytes. The activity of GPCR polypeptides can be assessed using a variety of in vitro and in vivo assays to determine functional, chemical, and physical effects, e.g., measuring ligand binding, (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Such assays can be used to test for inhibitors and activators of a GPCR. In particular, the assays can be used to test for compounds that modulate natural ligand-induced GPCR activity, for example, by modulating the binding of the natural ligand to the receptor and/or by modulating the ability of the natural ligand to activate the receptor. Typically in such assays, the test compound is contacted with the GPCR in the presence of the natural ligand. The natural ligand may be added to the assay before, after, or concurrently with the test compound. The results of the assay, for example, the level of binding, calcium mobilization, etc. is then compared to the level in a control assay that comprises the GPCR and natural ligand in the absence of the test compound.

Screening assays of the invention are used to identify modulators that can be used as therapeutic agents, e.g., antibodies to GPCRs and antagonists of GPCR activity.

The effects of test compounds upon the function of the GPCR polypeptides can be measured by examining any of the parameters described above. Any suitable physiological change that affects GPCR activity can be used to assess the influence of a test compound on the GPCRs and natural ligand-mediated GPCR activity. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$ or cAMP.

For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

The GPCR of the assay will be selected from a polypeptide having a sequence of SEQ ID NO:2, SEQ ID NO:4, SEQ ID NO:8, or SEQ ID NO:6, or conservatively modified variants thereof. Alternatively, the GPCR of the assay will be derived from a eukaryote and include an amino acid subsequence having amino acid sequence identity to SEQ ID NO:2, SEQ ID NO:4, SEQ ID NO:8 or SEQ ID NO:6. Generally, the amino acid sequence identity will be at least 70%, optionally at least 80%, optionally at least 90–95%. Optionally, the polypeptide of the assays will comprise or consist of a domain of a GPCR, such as an extracellular domain, transmembrane domain, cytoplasmic domain, ligand binding domain, subunit association domain, active site, and the like. Either a GPCR or a domain thereof can be covalently linked to a heterologous protein to create a chimeric protein used in the assays described herein.

Modulators of GPCR activity are tested using GPCR polypeptides as described above, either recombinant or naturally occurring. The protein can be isolated, expressed in a cell, expressed in a membrane derived from a cell, expressed in tissue or in an animal, either recombinant or naturally occurring. For example, adipocytes, cells of the immune system, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to a GPCR, a domain, or chimeric protein can be tested in a number of formats. binding can be performed in solution, in a bilayer membrane, attached to a solid phase, in a lipid monolayer, or in vesicles. Typically, in an assay of the invention, the binding of the natural ligand to its receptor is measured in the presence of a candidate modulator. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties. In some embodiments, the ability of a ligand to compete for binding of [$^3$H]-nicotinic acid to TGR4, often recombinant TGR4b or TGR183, as is directly measured in a binding assay.

Receptor-G-protein interactions can also be used to assay for modulators. For example, in the absence of GTP, binding of an activator such as the natural ligand will lead to the formation of a tight complex of a G protein (all three subunits) with the receptor. This complex can be detected in a variety of ways, as noted above. Such an assay can be modified to search for inhibitors. For example, the ligand can be added to the receptor and G protein in the absence of GTP to form a tight complex. Inhibitors may be identified by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by $G_q$ and other cognate G proteins, and modulation of diverse channels by Gi and other G proteins. Downstream consequences such as generation of diacyl glycerol and IP$_3$ by phospholipase C, and in turn, for calcium mobilization, e.g., by IP$_3$ (further discussed below) can also be examined. Thus, modulators can be evaluated for the ability to stimulate or inhibit ligand-mediated downstream effects. For example, nicotinic acid specifically activates TGR4, e.g., TGR4b, and TGR183 in calcium mobilization assays. Candidate modulators may be assessed for the ability to inhibit calcium mobilization induced by nicotinic acid or a related compound that activates the receptor.

In other examples, the ability of a test compound to activate a TGR4, e.g., TGR4b, or TGR183 can be determined using downstream assays such as measuring lipolysis in adipocytes, release of free fatty acids from adipose tissue, and lipoprotein lipase activity. This may be accomplished, for example, using a competition assay in which varying amounts of a test compound are incubated with a TGR4 or TGR183, typically a recombinant TGR4b or TGR183 and nicitonic acid.

Activated GPCRs become substrates for kinases that phosphorylate the C-terminal tail of the receptor (and possibly other sites as well). Thus, activators will promote the transfer of $^{32}$P from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors.

Modulators may therefore also be identified using assays involving β-arrestin recruitment. β-arrestin serves as a regulatory protein that is distributed throughout the cytoplasm in unactivated cells. Ligand binding to an appropriate GPCR is associated with redistribution of β-arrestin from the cytoplasm to the cell surface, where it associates with the GPCR. Thus, receptor activation and the effect of candidate modulators on ligand-induced receptor activation, can be assessed by monitoring β-arrestin recruitment to the cell surface. This is frequently performed by transfecting a labeled β-arrestin fusion protein (e.g., β-arrestin-green fluorescent protein (GFP)) into cells and monitoring its distribution using confocal microscopy (see, e.g., Groarke et al., J. Biol. Chem. 274(33):23263–69 (1999)).

Receptor internalization assays may also be used to assess receptor function. Upon ligand binding, the G-protein coupled receptor—ligand complex is internalized from the plasma membrane by a clathrin-coated vesicular endocytic process; internalization motifs on the receptors bind to adaptor protein complexes and mediate the recruitment of the activated receptors into clathrin-coated pits and vesicles. Because only activated receptors are internalized, it is possible to detect ligand-receptor binding by determining the amount of internalized receptor. In one assay format, cells are transiently transfected with radiolabeled receptor and incubated for an appropriate period of time to allow for ligand binding and receptor internalization. Thereafter, surface-bound radioactivity is removed by washing with an acid solution, the cells are solubilized, and the amount of internalized radioactivity is calculated as a percentage of ligand binding. See, e.g., Vrecl et al., Mol. Endocrinol. 12:1818–29 (1988) and Conway et al., J. Cell Physiol. 189(3):341–55 (2001). In addition, receptor internalization approaches have allowed real-time optical measurements of GPCR interactions with other cellular components in living cells (see, e.g., Barak et al., Mol. Pharmacol. 51(2)177–84 (1997)). Modulators may be identified by comparing receptor internalization levels in control cells and cells contacted with candidate compounds. For example, candidate modulators are assayed by examining their effects on receptor internalization upon binding of the natural ligand, e.g., nicotinic acid, to its cognate receptor, i.e., TGR4 or TGR183; respectively.

Another technology that can be used to evaluate GPCR-protein interactions in living cells involves bioluminescence resonance energy transfer (BRET). A detailed discussion regarding BRET can be found in Kroeger et al., J. Biol. Chem., 276(16):12736–43 (2001).

Receptor-stimulated guanosine 5'-O-(γ-Thio)-Triphosphate ([$^{35}$S]GTPγS) binding to G-proteins may also be used as an assay for evaluating modulators of GPCRs. [$^{35}$S] GTPγS is a radiolabeled GTP analog that has a high affinity for all types of G-proteins, is available with a high specific activity and, although unstable in the unbound form, is not hydrolyzed when bound to the G-protein. Thus, it is possible to quantitatively assess ligand-bound receptor by comparing stimulated versus unstimulated [$^{35}$S]GTPγS binding utilizing, for example, a liquid scintillation counter. Inhibitors of the receptor-ligand interactions would result in decreased [S]GTPγS binding. Descriptions of [$^{35}$S]GTPγS binding assays are provided in Traynor and Nahorski, *Mol. Pharmacol.* 47(4):848–54 (1995) and Bohn et al., *Nature* 408: 720–23 (2000).

The ability of modulators to affect ligand-induced ion flux may also be determined. Ion flux may be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

Preferred assays for G-protein coupled receptors include cells that are loaded with ion or voltage sensitive dyes to report receptor activity. Assays for determining activity of such receptors can also use known agonists and antagonists for other G-protein coupled receptors and the natural ligands disclosed herein as negative or positive controls to assess activity of tested compounds. In assays for identifying modulatory compounds (e.g., agonists, antagonists), changes in the level of ions in the cytoplasm or membrane voltage are monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., *Proc. Nat'l Acad. Sci. USA* 88:10049–10053 (1991)). Such promiscuous G-proteins allow coupling of a wide range of receptors to signal transduction pathways in heterologous cells.

As noted above, receptor activation by ligand binding typically initiates subsequent intracellular events, e.g., increases in second messengers such as IP$_3$, which releases intracellular stores of calcium ions. Activation of some G-protein coupled receptors stimulates the formation of inositol triphosphate (IP$_3$) through phospholipase C-mediated hydrolysis of phosphatidylinositol (Berridge & Irvine, *Nature* 312:315–21 (1984)). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated by ligand binding, result in a change in the level of intracellular cyclic nucleotides, e.g., cAMP or cGMP, by activating or inhibiting downstream effectors such as adenylate cyclase. Nicotinic acid inhibits adenylyl cyclase in adipocytes. In such a case, i.e., where activation of a TGR4 or TGR183 receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270: 15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Samples that are treated with a potential GPCR inhibitor or activator are compared to control samples comprising the natural ligand without the test compound to examine the extent of modulation. Control samples (untreated with activators or inhibitors) are assigned a relative GPCR activity value of 100. Inhibition of a GPCR is achieved when the GPCR activity value relative to the control is about 90%, optionally 50%, optionally 25–0%. Activation of a GPCR is achieved when the GPCR activity value relative to the control is 110%, optionally 150%, 200–500%, or 1000–2000%.

B. Modulators

The compounds tested as modulators of GPCRs can be any small chemical compound, or a biological entity, e.g., a macromolecule such as a protein, sugar, nucleic acid or lipid. Alternatively, modulators can be genetically altered versions of a GPCR. Typically, test compounds will be small chemical molecules and peptides. Essentially any chemical compound can be used as a potential modulator or ligand in the assays of the invention. Most often, compounds can be dissolved in aqueous or organic (especially DMSO-based) solutions. The assays are designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and are appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:9. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate GPCR activity involves computer assisted drug design, in which a computer system is used to generate a three-dimensional structure of GPCR based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify the regions that have the ability to bind, e.g., ligands. These regions are then used to identify various compounds that modulate ligand-receptor binding.

The three-dimensional structural model of the protein is generated by entering protein amino acid sequences of at least 10 amino acid residues or corresponding nucleic acid sequences encoding a GPCR polypeptide into the computer system. The amino acid sequence of the polypeptide or the nucleic acid encoding the polypeptide is selected from the group consisting of SEQ ID NO: 2, SEQ ID NO:4, SEQ ID NO:8, or SEQ ID NO:6, or SEQ ID NO: 1, SEQ ID NO:3, SEQ ID NO:7, or SEQ ID NO:5, respectively, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the GPCR protein to identify ligands that bind to GPCR. Binding affinity between the protein and ligands is determined using energy terms to determine which ligands have an enhanced probability of binding to the protein.

Computer systems are also used to screen for mutations, polymorphic variants, alleles and interspecies homologs of GPCR genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated GPCR genes involves receiving input of a first nucleic acid or amino acid sequence encoding an GPCR, selected from the group consisting of SEQ ID NO:1, SEQ ID NO:3, SEQ ID NO:7 or SEQ ID NO:5, or SEQ ID NO:2, SEQ ID NO:4, SEQ ID NO:8 or SEQ ID NO:6, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in GPCR genes, and mutations associated with disease states and genetic traits.

E. Expression Assays

Certain screening methods involve screening for a compound that modulates the expression of the GPCRs described herein, or the levels of natural ligands, e.g., niacin. Such methods generally involve conducting cell-based assays in which test compounds are contacted with one or more cells expressing the GPCR or ligand and then detecting an increase or decrease in expression (either transcript or translation product). Such assays are typically performed with cells that express the endogenous GPCR or ligand.

Expression can be detected in a number of different ways. As described herein, the expression levels of the protein in a cell can be determined by probing the mRNA expressed in a cell with a probe that specifically hybridizes with a transcript (or complementary nucleic acid derived therefrom) of the GPCR or protein ligand. Probing can be conducted by lysing the cells and conducting Northern blots or without lysing the cells using in situ-hybridization techniques (see above). Alternatively, protein can be detected using immunological methods in which a cell lysate is probed with antibodies that specifically bind to the protein.

Other cell-based assays are reporter assays conducted with cells that do not express the protein. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase), luciferase, β-galactosidase and alkaline phosphatase.

In these assays, cells harboring the reporter construct are contacted with a test compound. A test compound that either modulates the activity of the promoter by binding to it or triggers a cascade that produces a molecule that modulates the promoter causes expression of the detectable reporter. Certain other reporter assays are conducted with cells that harbor a heterologous construct that includes a transcriptional control element that activates expression of the GPCR or ligand and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

Kits

GPCRs, e.g., recombinant GPCRs, and their homologs are a useful tool for identifying cells such as immune cells or adipose cells, for forensics and paternity determinations, for diagnosing diseases, and for examining signal transduction. GPCR-specific reagents that specifically bind to a GPCR protein, e.g., nicotinic acid, or GPCR antibodies are used to examine signal transduction regulation.

The present invention also provides for kits for screening for modulators of ligand-GPCR interactions. Such kits can be prepared from readily available materials and reagents. For example, such kits can comprise any one or more of the following materials: a GPCR, typically a recombinant GPCR, reaction tubes, a nicotinic acid reagent, and instructions for testing GPCR activity. Optionally, the kit contains biologically active GPCR. A wide variety of kits and components can be prepared according to the present invention, depending upon the intended user of the kit and the particular needs of the user.

Disease Treatment and Diagnosis

In certain embodiments, TGR4 and TGR183 can be used in the diagnosis and treatment of certain diseases or conditions, i.e., TGR-associated disorders. For example, TGR4 or TGR183 are preferentially expressed in particular cell types (e.g., an adipocyte or an immune cell). Accordingly, these TGRs can be used to modulate cellular function and pathways that involve that cell type (e.g., responsiveness to extracellular signals, such as inflammatory signals; or metabolic pathways, such as lipid metabolism). TGR4 and TGR183 are preferentially expressed in adipocytes. Thus, TGR4, e.g., TGR4b, or TGR183 modulators, e.g., nicotinic acid, nicotinic acid analogs, or other compounds that have the ability to compete with nicotinic acid for binding to TGR4, e.g., TGR4b, or TGR183, or compounds that otherwise modulate nicotinic acid binding or nicotinic acid-induced activity, may be used for the treatment of disorders that involve lipid metabolism, e.g., hyperlipidemia, low HDL levels, or other disorders of fat metabolism, including disorders such as cardiovascular disease, stroke, diabetes, obesity, etc. (see, e.g., *Harrison's Principles of Internal Medicine,* 12th Edition, Wilson, et al., eds., McGraw-Hill, Inc.). In some embodiments, TGR4 or TGR183 agonists may be used to treat lipid abnormalities.

Similarly, TGR4 is preferentially expressed in immune tissue, e.g., bone marrow, leukocytes, e.g., neutrophils and monocytes, and spleen. Thus, modulators of TGR4 activity may be used to treat diseases or conditions associated with the immune system and inflammatory responses, e.g., vascular disease, autoimmune disease, and various malignancies of the immune system (see, e.g., *Harrison's Principles of Internal Medicine,* 12th Edition, Wilson, et al., eds., McGraw-Hill, Inc.). For example, syndromes that includes an immune and/or inflammatory component include chronic inflammatory diseases including, but not limited to, connective tissue disorders, e.g., osteoarthritis, multiple sclerosis, Guillain-Barre syndrome, Crohn's disease, inflammatory bowel disease, ulcerative colitis, psoriasis, graft versus host disease, systemic lupus erythematosus, autoimmune thyroiditis, allergies, and insulin-dependent diabetes mellitus. Other inflammatory and autoimmune diseases include diseases due to oxidative or ischemic injury, e.g., damage to blood vessels; asthma, inflammation of the skin, eyes, or joints, e.g., ankylosing spondylitis, psoriasis, sclerosing cholangitis; and other autoimmune diseases (see, e.g., *Harrison's Principles of Internal Medicine,* supra). Further, infectious diseases causes by viral, bacterial, fungal or other infection may be treatable using a modulator of TGR4. Further, a TGR4 modulator may also be used to treat allergic reactions and conditions (e.g., anaphylaxis or food allergies). Further, splenic enlargement, anemias, and various malignancies *Harrison's Principles of Internal Medicine,* supra, may also be treated using TGR4 modulators identified as described herein.

In some embodiments, TGR4 antagonists, e.g., antibodies or molecules that neutralize nicotinic acid function mediated through TGR4b, may be used to treat inflammatory type conditions.

Further, dysfunction in TGR4 or TGR183 or in the levels of the ligands that bind to the GPCRs may produce a disease, condition, or symptom associated with a lack of function of the particular cell type in which the GPCR is expressed. As noted above, TGR4 and TGR183 are preferentially expressed in adipocytes. Thus, mutation or dysregulation of these GPCRs can lead to disorders relating to lipid metabolism, including weight control and hyperlipidemia. TGR4 and TGR183 sequences may therefore also be used to detect, or diagnose a propensity for, conditions such as high levels of LDL, obesity, or various other disorders of fat metabolism. Similarly, mutations or dysregulation of TGR4, which is preferentially expressed in immune tissue, may lead to malignancies, anemia, spleen-associated disorders or conditions, e.g., splenic enlargement, blood disorders, and other disorders of immune function such as autoimmune diseases. TGR4 sequences may therefore be used to detect, or diagnose a propensity for, these various immune tissue-associated disorders.

Accordingly, the methods of the invention can be used to diagnose any of the herein-described disorders or conditions in a patient, e.g., by examining the sequence, level, or activity of any of the present GPCRs in a patient, wherein an alteration, e.g., a decrease, in the level of expression or activity in a GPCR, or the detection of a deleterious mutation in a GPCR, indicates the presence or the likelihood of the disease or condition. Further, as described above, modulation of the TGR4 and/or TGR183 (e.g., by administering modulators of the GPCR) can be used to treat or prevent any of the conditions or diseases.

Administration and Pharmaceutical Compositions

Modulators of the GPCR—ligand interaction can be administered to a mammalian subject for modulation of signal transduction in vivo, e.g., for the treatment of any of the diseases or conditions described supra. As described in detail below, the modulators are administered in any suitable manner, optionally with pharmaceutically acceptable carriers.

The identified modulators can be administered to a patient at therapeutically effective doses to prevent, treat, or control diseases and disorders mediated, in whole or in part, by a GPCR-ligand interaction of the present invention. The compositions are administered to a patient in an amount sufficient to elicit an effective protective or therapeutic response in the patient. An amount adequate to accomplish this is defined as "therapeutically effective dose." The dose will be determined by the efficacy of the particular GPCR modulators employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

EXAMPLES

The following examples are provided by way of illustration only and not by way of limitation. Those of skill in the art will readily recognize a variety of noncritical parameters that could be changed or modified to yield essentially similar results.

Two GPCR receptors were identified as having nicotinic acid as a natural ligand. Alignment of the TGR4 and TGR183 amino acid sequences showed that the polypeptides were 50% identical.

Example 1

Identification of Nicotinic Acid as a Ligand for TGR4 and TGR183

Nicotinic acid was identified as a ligand for TGR4 and TGR183 in an Aequorin assay for intracellular [$Ca^{2+}$] (see, e.g., Stables et al., *Anal. Biochem.* 252:115–126, 1997). Aequorin catalyses the oxidation of coelenterazine, but only in the presence of $Ca^{2+}$ ions and thus can be used as an indicator of intracellular calcium levels. Briefly, the assays were performed using the following methodology.

Figure 3:
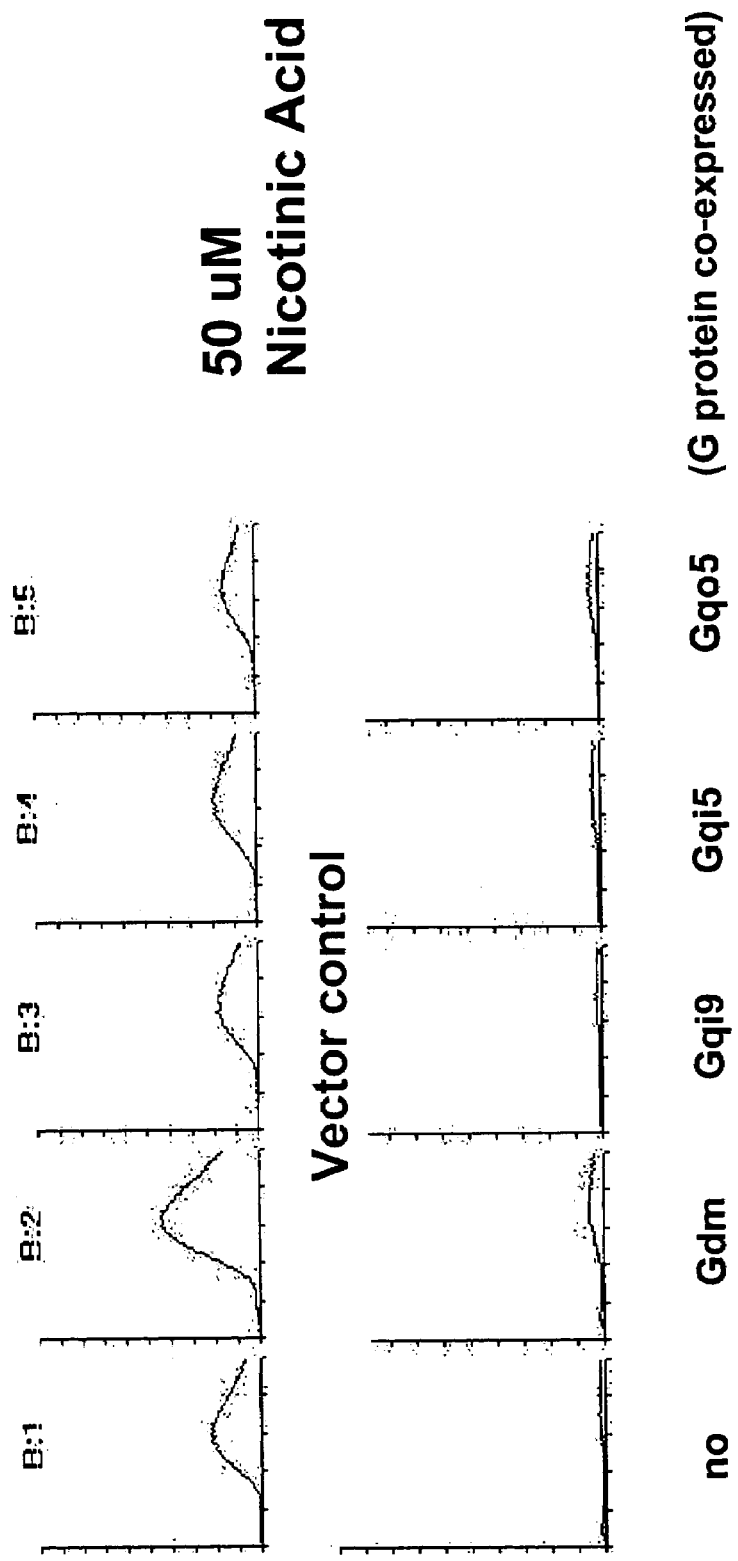
FIG. 3 shows the results of an Aequorin assay, which demonstrates that nicotinic acid activates TGR183.

CHO cells were transiently transfected with expression plasmids encoding TGR4b or TGR183 together with a plasmid encoding mitochondria-targeting apoaequorin. The plasmids were co-transfected with chimeric G protein Gαqi9, which has the C-terminal 9 amino acids from the Gαq protein replaced with the C-terminal 9 amino acids form the Gαi protein. Cells were harvested 24 hr later and loaded with coelenterazine for 2 hr at 37 C. Aequorin assay was performed on MicroLumat 96 luminometer (Perkin Elmer). The results showed that nicotinic acid stimulated a TGR4-mediated increase in intracellular calcium in a concentration dependent manner with an $EC_{50}$ of around 340 nM (FIG. 2). At a concentration of 50 μM, nicotinic acid also stimulated a TGR183-mediated increase in intracellular calcium (FIG. 3).

Figure 4:
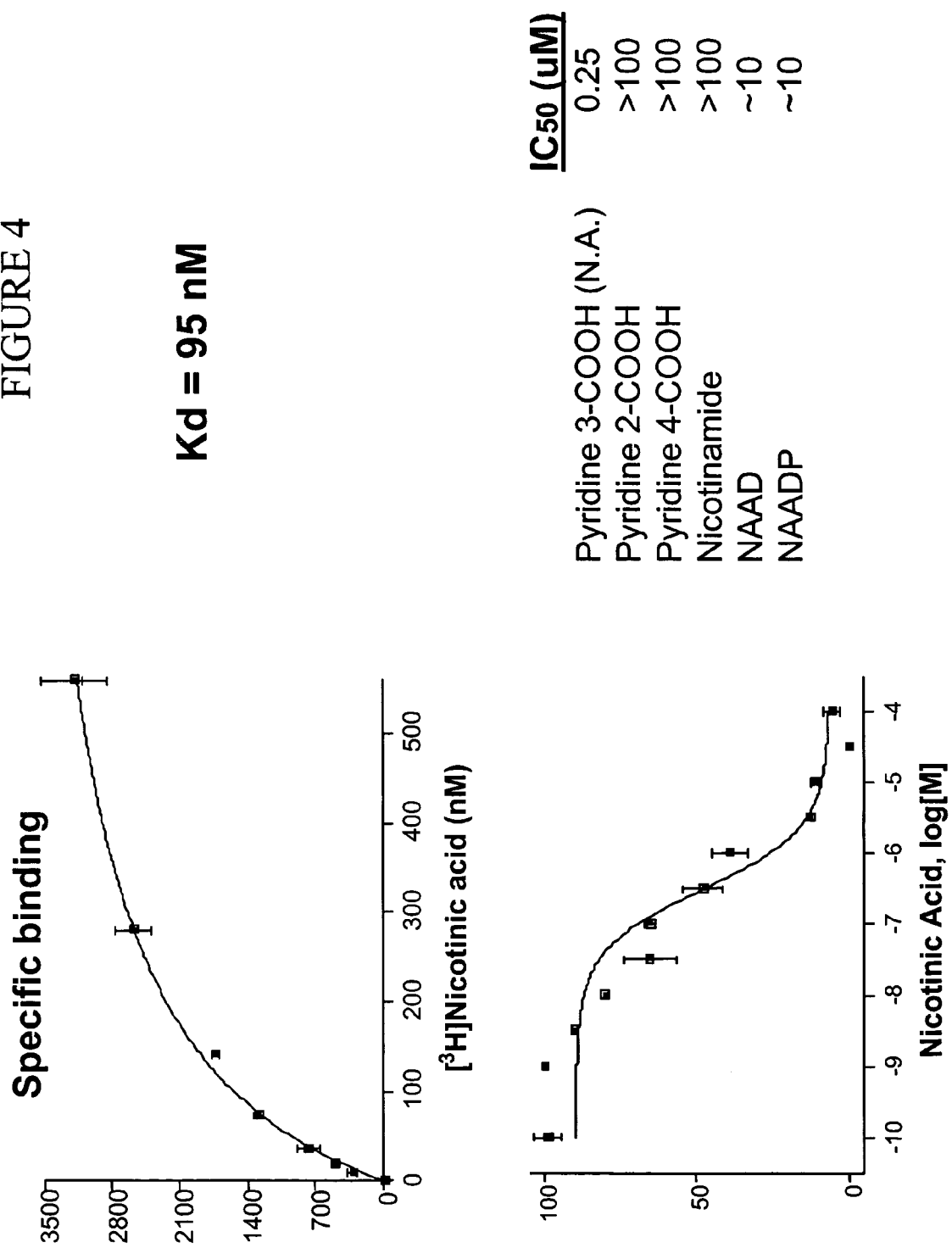
FIG. 4 shows that nicotinic acid binds TGR4.

Nicotinic acid binding to TGR4 was also evaluated. Briefly, HEK293T cells were transfected with expression plasmids for TGR4b. Forty-eight hours later, cells were harvested and resuspended in hypotonic lysis buffer (50 mM Tris-HCl, pH7.4, 1 mM $MgCl_2$, 10 mM NaCl, 1 mM DTT and protease inhibitor cocktail). Cell membranes were prepared by homogenization of cells in a glass homgenizer. The homogenates were centrifuged for 10 min at 1000×g. The supernatants were collected and centrifuged again at 100,000×g for 1 hr. The pellets were resuspended and used in binding assays. Equilibrium binding of [$^3$H]-nicotinic acid to membranes was done with 25 μg membrane protein in a total volume of 200 μl in 50 mM Tris-HCl, pH 7.4 containing 0.02% CHAPS. Non-specific binding was performed in the presence of 200 μM nicotinic acid. The reaction was incubated at 4° C. for 2 hrs. Separation of membrane bound from unbound [$^3$H]-nicotinic acid was done by filtration of the samples through Whatman GF-B filters with 5 times washing step each with 300 μl of 50 mM Tris-HCl (pH 7.4). Radioactivity was counted on a scintillation counter. The results of the experiment showed that nicotinic acid specifically binds TGR4 (FIG. 4).

Example 2

Expression of TGR4 and TGR183

TGR4 and TGR183 expression in adipocytes and human cells was evaluated using RT-PCR. Total RNAs were isolated from human and mouse cells by Trizol reagent. RNA samples were treated with DNase and RT-PCR reaction was performed by using the One-step RT-PCR kit (Applied Biosystems). PCR reaction was performed for 33 cycles (each cycle has 94° C. for 1 min, 55° C. for 1 min, and 72° C. for 1 min). PCR reaction products were run on 2% agarose gel. TGR183 is expressed in primary human adipocytes as well as cultured human pre-adipocytes and adipocytes. TGR183 is also expressed in differentiated mouse adipocytes (FIG. 5). TGR4 is also expressed in human primary adipocytes as well as cultured human pre-adipocytes and adipocytes (FIG. 6). TGR4 is also expressed in differentiated mouse adipocytes as well as preadipocytes.

Figure 7:
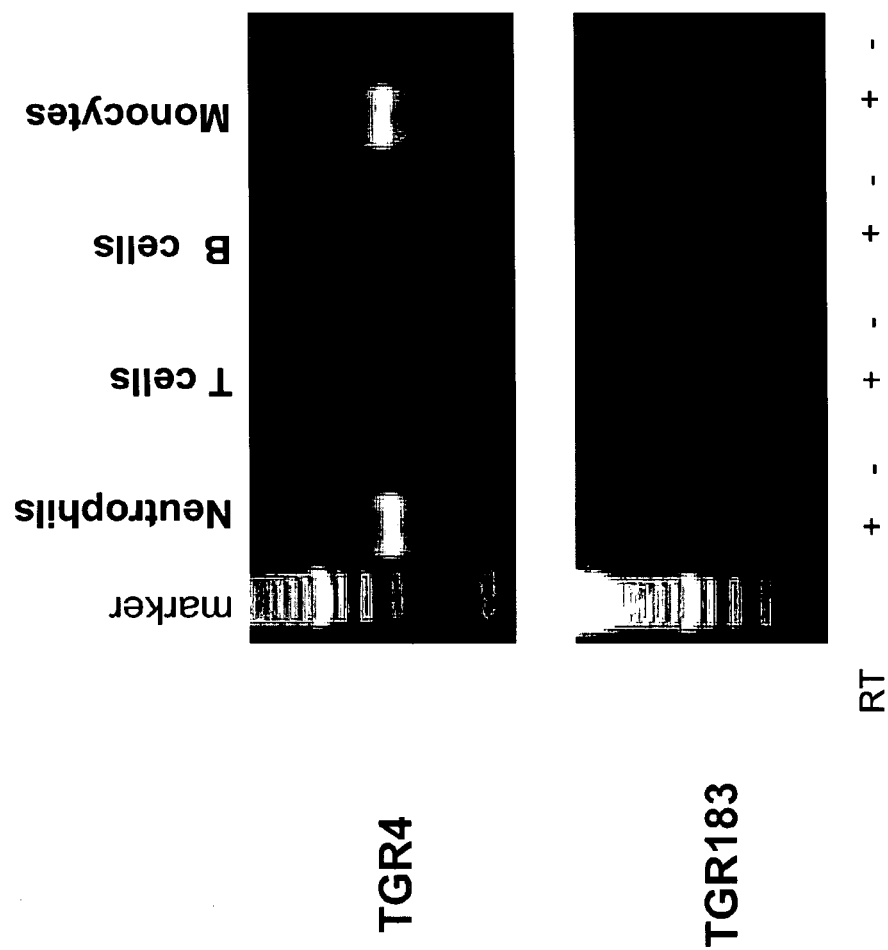
FIG. 7 shows the differential expression between TGR4 and TGR183 in human primary immune cells.

Expression was also analyzed in human primary immune cells. TGR4 was expressed in neutrophils and monocytes whereas TGR183 was not (FIG. 7).

TGR4 and TGR183 expression was also evaluated in various tissues by northern blot analysis. Briefly, nylon membranes containing polyA$^+$ RNAs from various tissues were hybridized with $^{32}$P-labeled cDNAs encoding the full-length TGR4 or TGR183 under high stringency conditions using Rapid-Hyb™ solution (Amersham) at 65° C. After overnight hybridization, membranes were washed with 0.1×SSC, 0.5% SDS at 65° C. for 2–3 hr, before being exposed to X-ray film for overnight. The results are shown in FIG. 8. TGR4 was detected in various tissues including spleen, lung, leukocytes, bone marrow and fetal liver. TGR183 was not detectable by northern blot in these tissues.

Example 3

Nicotinic Acid Analogs Activate TGR4

The ability of nicotinic acid analogs to bind and activate TGR4b was also evaluated. The following analogs were tested: nicotinoyl chloride, pyridazine 4-carboxylic acid; 3-pyridineacetic acid, 5-methyl-2-pyrazinecarboxylic acid-4-oxide (Acipimox), 2-pyrazinecarboxylic acid, and 5-fluoro nicotinic acid. Nicotinic acid and analog binding was assessed as described in Example 1. Lipolysis activity was assessed using known assays (*Obesity Research* 10:266–9, 2002; *Endocrinology* 140:398–404, 1999). Briefly, human adipocytes in 96-well plates were treated with 0.5 μM Forskolin together with different concentrations of nicotinic acid (or analogs) in 150 μl assay buffer. Sixteen hours later, a sample (100 μl) was collected and transferred to a fresh plate. Glycerol concentration in the samples, which represents the amount of adipocyte lipolysis, was measured using reagents from ZenBio.

The results (Table 1) show that nicotinyl chloride, which is readily hydrolyzed to nicotinic acid, has agonist and binding activity similar to that of nicotinic acid. The analog 3-pyridineacetic acid, in which the carboxylic acid in nicitonic acid is replaced by acetic acid, also exhibits activity. Pyridazine 4-carboxylic acid and 2-pyrazinecarboxylic acid, which are compounds in which one carbon in the pyridine ring of nicitonic acid is replaced with nitrogen, are also active in binding and activity assays. Acipimox has a potency 20–50 times lower than nicotinic acid on TGR4. Substitution at the 5 position on the pyridine ring (5-fluoro nicotinic acid) gives rise to a much lower potency. Nicotinamide, the other form of vitamin B3 devoid of the lipid-lowering activity, is completely inactive on TGR4b.

TABLE 1 activities of nicotinic acid analogs in TGR4 binding, TGR4-induced aequorin luminescence, and inhibition of forskolin-stimulated lipolysis of human adipocytes (mM)

| Chemical Name | $EC_{50}$ (Aequorin) | $IC_{50}$ (binding) | $EC_{50}$ (anti-lipolysis) |
|---|---|---|---|
| nicotinic acid (3-pyridinecarboxylic acid) | 0.38 | 0.16 | 0.062 |
| nicotinoyl chloride HCl | 0.61 | 0.25 | 0.15 |
| Pyridazine 4-carboxylic acid | 4.5 | 3.0 | 2.8 |
| 3-pyridineacetic acid HCl | 4.8 | 7.5 | 0.77 |
| 5-methyl-2-pyrazinecarboxylic acid-4-oxide (Acipimox) | 6.9 | 9.1 | 6.0 |
| 2-pyrazinecarboxylic acid | 8.6 | 17 | 6.5 |
| 5-fluoro nicotinic acid | 30 | 15 | nd |

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE OF SEQUENCES

SEQ ID NO:1 TGR4a nucleic acid sequence
ATGAATCGGCACCATCTGCAGGATCACTTTCTGGAAATAGACAAGAAGAACTGCTGTGTGTTCCGAGA

TGACTTCATTGCCAAGGTGTTGCCGCCGGTGTTGGGGCTGGAGTTTATCTTTGGGCTTCTGGGCAATG

GCCTTGCCCTGTGGATTTTCTGTTTCCACCTCAAGTCCTGGAAATCCAGCCGGATTTTCCTGTTCAAC

CTGGCAGTAGCTGACTTTCTACTGATCATCTGCCTGCCGTTCGTGATGGACTACTATGTGCGGCGTTC

AGACTGGAACTTTGGGGACATCCCTTGCCGGCTGGTGCTCTTCATGTTTGCCATGAACCGCCAGGGCA

GCATCATCTTCCTCACGGTGGTGGCGGTAGACAGGTATTTCCGGGTGGTCCATCCCCACCACGCCCTG

AACAAGATCTCCAATTGGACAGCAGCCATCATCTCTTGCCTTCTGTGGGGCATCACTGTTGGCCTAAC

-continued

TABLE OF SEQUENCES

AGTCCACCTCCTGAAGAAGAAGTTGCTGATCCAGAATGGCCCTGCAAATGTGTGCATCAGCTTCAGCA

TCTGCCATACCTTCCGGTGGCACGAAGCTATGTTCCTCCTGGAGTTCCTCCTGCCCCTGGGCATCATC

CTGTTCTGCTCAGCCAGAATTATCTGGAGCCTGCGGCAGAGACAAATGGACCGGCATGCCAAGATCAA

GAGAGCCATCACCTTCATCATGGTGGTGGCCATCGTCTTTGTCATCTGCTTCCTTCCCAGCGTGGTTG

TGCGGATCCGCATCTTCTGGCTCCTGCACACTTCGGGCACGCAGAATTGTGAAGTGTACCGCTCGGTG

GACCTGGCGTTCTTTATCACTCTCAGCTTCACCTACATGAACAGCATGCTGGACCCCGTGGTGTACTA

CTTCTCCAGCCCATCCTTTCCCAACTTCTTCTCCACTTTGATCAACCGCTGCCTCCAGAGGAAGATGA

CAGGTGAGCCAGATAATAACCGCAGCACGAGCGTCGAGCTCACAGGGGACCCCAACAAAACCAGAGGC

GCTCCAGAGGCGTTAATGGCCAACTCCGGTGAGCCATGGAGCCCCTCTTATCTGGGCCCAACCTCAAA

TAACCATTCCAAGAAGGGACATTGTCACCAAGAACCAGCATCTCTGGAGAAACAGTTGGGCTGTTGCA

TCGAGTAA

SEQ ID NO:2 TGR4a polypeptide sequence
MNRHHLQDHFLEIDKKNCCVFRDDFIAKVLPPVLGLEFIFGLLGNGLALWIFCFHLKSWKSSRIFLFN

LAVADFLLIICLPFVMDYYVRRSDWNFGDIPCRLVLFMFAMNRQGSIIFLTVVAVDRYFRVVHPHHAL

NKISNWTAAIISCLLWGITVGLTVHLLKKKLLIQNGPANVCISFSICHTFRWHEAMFLLEFLLPLGII

LFCSARIIWSLRQRQMDRHAKIKRAITFIMVVAIVFVICFLPSVVVRIRIFWLLHTSGTQNCEVYRSV

DLAFFITLSFTYMNSMLDPVVYYFSSPSFPNFFSTLINRCLQRKMTGEPDNNRSTSVELTGDPNKTRG

APEALMANSGEPWSPSYLGPTSNNHSKKGHCHQEPASLEKQLGCCIE

SEQ ID NO:3 TGR4b nucleic acid sequence
ATGAATCGGCACCATCTGCAGGATCACTTTCTGGAAATAGACAAGAAGAACTGCTGTGTGTTCCGAGA

TGACTTCATTGTCAAGGTGTTGCCGCCGGTGTTGGGGCTGGAGTTTATCTTCGGGCTTCTGGGCAATG

GCCTTGCCCTGTGGATTTTCTGTTTCCACCTCAAGTCCTGGAAATCCAGCCGGATTTTCCTGTTCAAC

CTGGCAGTGGCTGACTTTCTACTGATCATCTGCCTGCCCTTCCTGATGGACAACTATGTGAGGCGTTG

GGACTGGAAGTTTGGGGACATCCCTTGCCGGCTGATGCTCTTCATGTTGGCTATGAACCGCCAGGGCA

GCATCATCTTCCTCACGGTGGTGGCGGTAGACAGGTATTTCCGGGTGGTCCATCCCCACCACGCCCTG

AACAAGATCTCCAATCGGACAGCAGCCATCATCTCTTGCCTTCTGTGGGCATCACTATTGGCCTGAC

AGTCCACCTCCTGAAGAAGAAGATGCCGATCCAGAATGGCGGTGCAAATTTGTGCAGCAGCTTCAGCA

TCTGCCATACCTTCCAGTGGCACGAAGCCATGTTCCTCCTGGAGTTCTTCCTGCCCCTGGGCATCATC

CTGTTCTGCTCAGCCAGAATTATCTGGAGCCTGCGGCAGAGACAAATGGACCGGCATGCCAAGATCAA

GAGAGCCATCACCTTCATCATGGTGGTGGCCATCGTCTTTGTCATCTGCTTCCTTCCCAGCGTGGTTG

TGCGGATCCGCATCTTCTGGCTCCTGCACACTTCGGGCACGCAGAATTGTGAAGTGTACCGCTCGGTG

GACCTGGCGTTCTTTATCACTCTCAGCTTCACCTACATGAACAGCATGCTGGACCCCGTGGTGTACTA

CTTCTCCAGCCCATCCTTTCCCAACTTCTTCTCCACTTTGATCAACCGCTGCCTCCAGAGGAAGATGA

CAGGTGAGCCAGATAATAACCGCAGCACGAGCGTCGAGCTCACAGGGGACCCCAACAAAACCAGAGGC

GCTCCAGAGGCGTTAATGGCCAACTCCGGTGAGCCATGGAGCCCCTCTTATCTGGGCCCAACCTCTCC

TTAA

SEQ ID NO:4 TGR4b amino acid sequence
MNRHHLQDHFLEIDKKNCCVFRDDFIVKVLPPVLGLEFIFGLLGNGLAGWIFCFHLKSWKSSRIFLFN

LAVADFLLIICLPFLMDNYVRRWDWKFGDIPCRLMLFMLAMNRQGSIIFLTVVAVDRYFRVVHPHHAL

NKISNRTAAIISCLLWGITIGLTVHLLKKKMPIQNGGANLCSSFSICHTFQWHEAMFLLEFFLPLGII

TABLE OF SEQUENCES

LFCSARIIWSLRQRQMDRHAKIKRAITFIMVVAIVFVICFLPSVVVRIRIFWLLHTSGTQNCEVYRSV

DLAFFITLSFTYMNSMLDPVVYYFSSPSFPNFFSTLINRCLQRKMTGEPDNNRSTSVELTGDPNKTRG

APEALMANSGEPWSPSYLGPTSP

SEQ ID NO:5 TGR183 nucleic acid sequence
ATGTACAACGGGTCGTGCTGCCGCATCGAGGGGGACACCATCTCCCAGGTGATGCCGCCGCTGCTCAT

TGTGGCCTTTGTGCTGGGCGCACTAGGCAATGGGGTCGCCCTGTGTGGTTTCTGCTTCCACATGAAGA

CCTGGAAGCCCAGCACTGTTTACCTTTTCAATTTGGCCGTGGCTGATTTCCTCCTTATGATCTGCCTG

CCTTTTCGGACAGACTATTACCTCAGACGTAGACACTGGGCTTTTGGGGACATTCCCTGCCGAGTGGG

GCTCTTCACGTTGGCCATGAACAGGGCCGGGAGCATCGTGTTCCTTACGGTGGTGGCTGCGGACAGGT

ATTTCAAAGTGGTCCACCCCCACCACGCGGTGAACACTATCTCCACCCGGGTGGCGGCTGGCATCGTC

TGCACCCTGTGGGCCCTGGTCATCCTGGGAACAGTGTATCTTTTGCTGGAGAACCATCTCTGCGTGCA

AGAGACGGCCGTCTCCTGTGAGAGCTTCATCATGGAGTCGGCCAATGGCTGGCATGACATCATGTTCC

AGCTGGAGTTCTTTATGCCCCTCGGCATCATCTTATTTTGCTCCTTCAAGATTGTTTGGAGCCTGAGG

CGGAGGCAGCAGCTGGCCAGACAGGCTCGGATGAAGAAGGCGACCCGGTTCATCATGGTGGTGGCAAT

TGTGTTCATCACATGCTACCTGCCCAGCGTGTCTGCTAGACTCTATTTCCTCTGGACGGTGCCCTCGA

GTGCCTGCGATCCCTCTGTCCATGGGGCCCTGCACATAACCCTCAGCTTCACCTACATGAACAGCATG

CTGGATCCCCTGGTGTATTATTTTTCAAGCCCCTCCTTTCCCAAATTCTACAACAAGCTCAAATCTG

CAGTCTGAAACCCAAGCAGCCAGGACACTCAAAAACACAAAGGCCGGAAGAGATGCCAATTTCGAACC

TCGGTCGCAGGAGTTGCATCAGTGTGGCAAATAGTTTCCAAAGCCAGTCTGATGGGCAATGGGATCCC

CACATTGTTGAGTGGCACTGA

SEQ ID NO:6 TGR 183 amino acid sequence
MYNGSCCRIEGDTISQVMPPLLIVAFVLGALGNGVALCGFCFHMKTWKPSTVYLFNLAVADFLLMICL

PFRTDYYLRRRHWAFGDIPCRVGLFTLAMNRAGSIVFLTVVAADRYFKVVHPHHAVNTISTRVAAGIV

CTLWALVILGTVYLLLENHLCVQETAVSCESFIMESANGWHDIMFQLEFFMPLGIILFCSFKIVWSLR

RRQQLARQARMKKATRFIMVVAIVFITCYLPSVSARLYFLWTVPSSACDPSVHGALHITLSFTYMNSM

LDPLVYYFSSPSFPKFYNKLKICSLKPKQPGHSKTQRPEEMPISNLGRRSCISVANSFQSQSDGQWDP

HIVEWH

SEQ ID NO:7 TGR4a allele 2 nucleic acid sequence
ATGAATCGGCACCATCTGCAGGATCACTTTCTGGAAATAGACAAGAAGAACTGCTGTGTGTTCCGAGA

TGACTTCATTGCCAAGGTGTTGCCGCCGGTGTTGGGGCTGGAGTTTATCTTTGGGCTTCTGGGCAATG

GCCTTGCCCTGTGGATTTTCTGTTTCCACCTCAAGTCCTGGAAATCCAGCCGGATTTTCCTGTTCAAC

CTGGCAGTAGCTGACTTTCTACTGATCATCTGCCTGCCGTTCGTGATGGACTACTATGTGCGGCGTTC

AGACTGGAAGTTTGGGGACATCCCTTGCCGGCTGGTGCTCTTCATGTTTGCCATGAACCGCCAGGGCA

GCATCATCTTCCTCACGGTGGTGGCGGTAGACAGGTATTTCCGGGTGGTCCATCCCCACCACGCCCTG

AACAAGATCTCCAATTGGACAGCAGCCATCATCTCTTGCCTTCTGTGGGCATCACTGTTGGCCTAAC

AGTCCACCTCCTGAAGAAGAAGTTGCTGATCCAGAATGGCCCTGCAAATGTGTGCATCAGCTTCAGCA

TCTGCCATACCTTCCGGTGGCACGAAGCTATGTTCCTCCTGGAGTTCCTCCTGCCCCTGGGCATCATC

CTGTTCTGCTCAGCCAGAATTATCTGGAGCCTGCGGCAGAGACAAATGGACCGGCATGCCAAGATCAA

GAGAGCCATCACCTTCATCATGGTGGTGGCCATCGTCTTTGTCATCTGCTTCCTTCCCAGCGTGGTTG

TGCGGATCCGCATCTTCTGGCTCCTGCACACTTCGGGCACGCAGAATTGTGAAGTGTACCGCTCGGTG

-continued

TABLE OF SEQUENCES

GACCTGGCGTTCTTTATCACTCTCAGCTTCACCTACATGAACAGCATGCTGGACCCCGTGGTGTACTA

CTTCTCCAGCCCATCCTTTCCCAACTTCTTCTCCACTTTGATCAACCGCTGCCTCCAGAGGAAGATGA

CAGGTGAGCCAGATAATAACCGCAGCACGAGCGTCGAGCTCACAGGGGACCCCAACAAAACCAGAGGC

GCTCCAGAGGCGTTAATGGCCAACTCCGGTGAGCCATGGAGCCCCTCTTATCTGGGCCCAACCTCAAA

TAACCATTCCAAGAAGGGACATTGTCACCAAGAACCAGCATCTCTGGAGAAACAGTTGGGCTGTTGCA

TCGAGTAA

SEQ ID NO:8 TGR4a allele 2 amino acid sequence
MNRHHLQDHFLEIDKKNCCVFRDDFIAKVLPPVLGLEFIFGLLGNGLALWIFCFHLKSWKSSRIFLFN

LAVADFLLIICLPFVMDYYVRRSDWKFGDIPCRLVLFMFAMNRQGSIIFLTVVAVDRYFRVVHPHHAL

NKISNWTAAIISCLLWGITVGLTVHLLKKKLLIQNGPANVCISFSICHTFRWHEAMFLLEFLLPLGII

LFCSARIIWSLRQRQMDRHAKIKRAITFIMVVAIVFVICFLPSVVVRIRIFWLLHTSGTQNCEVYRSV

DLAFFITLSFTYMNSMLDPVVYYFSSPSFPNFFSTLINRCLQRKMTGEPDNNRSTSVELTGDPNKTRG

APEALMANSGEPWSPSYLGPTSNNHSKKGHCHQEPASLEKQLGCCIE

What is claimed is:

1. A method of identifying a modulator of a polypeptide that has G-protein coupled receptor activity, is activated by nicotinic acid, and comprises the amino acid sequence of SEQ ID NO:6; wherein the method comprises:
  contacting a compound with said polypeptide; and
  determining the level of binding of nicotinic acid to the polypeptide in comparison to the level of binding between nicotinic acid and said polypeptide in an absence of said compound.

2. The method of claim 1, wherein the step of determining the level of binding comprises detecting nicotinic acid binding in a competitive binding assay.

3. The method of claim 1, wherein the step of determining the level of binding comprises detecting an alteration in a nicotinic acid-induced activity of said polypeptide.

4. The method of claim 3, wherein the nicotinic acid-induced activity is an increase in intracellular calcium.

* * * * *